(12) United States Patent
Plater-Zyberk

(10) Patent No.: US 9,353,180 B2
(45) Date of Patent: May 31, 2016

(54) METHOD OF TREATMENT BY THE ADMINISTRATION OF INHIBITORS OF GM-CSF AND IL-17

(75) Inventor: Christine Plater-Zyberk, Yvoire (FR)

(73) Assignee: AMGEN RESEARCH (MUNICH) GMBH, Munich (DE)

(*) Notice: Subject to any disclaimer, the term of this patent is extended or adjusted under 35 U.S.C. 154(b) by 100 days.

(21) Appl. No.: 12/990,006

(22) PCT Filed: Apr. 28, 2009

(86) PCT No.: PCT/EP2009/055129
§ 371 (c)(1),
(2), (4) Date: Dec. 14, 2010

(87) PCT Pub. No.: WO2009/133103
PCT Pub. Date: Nov. 5, 2009

(65) Prior Publication Data
US 2011/0104172 A1     May 5, 2011

Related U.S. Application Data

(60) Provisional application No. 61/125,880, filed on Apr. 29, 2008.

(51) Int. Cl.
*A61K 39/395* (2006.01)
*C07K 16/24* (2006.01)
*A61K 39/00* (2006.01)

(52) U.S. Cl.
CPC ............ *C07K 16/244* (2013.01); *C07K 16/243* (2013.01); *A61K 2039/507* (2013.01); *C07K 2317/34* (2013.01); *C07K 2317/76* (2013.01)

(58) Field of Classification Search
None
See application file for complete search history.

(56) References Cited

U.S. PATENT DOCUMENTS

| | | | | |
|---|---|---|---|---|
| 6,309,636 | B1* | 10/2001 | do Couto et al. | .......... 424/133.1 |
| 7,741,450 | B2 | 6/2010 | Sass et al. | |
| 7,807,155 | B2* | 10/2010 | Di Padova et al. | ......... 424/130.1 |
| 8,318,168 | B2 | 11/2012 | Sass et al. | |
| 8,623,364 | B2 | 1/2014 | Sass et al. | |
| 2014/0086928 | A1 | 3/2014 | Sass et al. | |

FOREIGN PATENT DOCUMENTS

| CN | 101001645 A | | 7/2007 |
|---|---|---|---|
| WO | WO 2006/013107 | * | 2/2006 |
| WO | WO-2006/013107 A1 | | 2/2006 |
| WO | WO-2006/066088 A2 | | 6/2006 |
| WO | WO 2006/111353 | * | 10/2006 |
| WO | WO-2006/111353 A2 | | 10/2006 |

OTHER PUBLICATIONS

MacCallum et al. Antibody-antigen Interactions: Contact Analysis and Binding Site Topography. J. Mol. Biol., 1996, 262:732-745.*
Padlan et al. Structure of an antibody-antigen complex: Crystal structure of the HyHEL-10 Fab-lysozyme complex. Proc. Natl. Acad. Sci. USA, 1989, 86 : 5938-5942.*
Crane et al. Cytokine regulation of granulocyte-macrophage colony-stimulating factor (GM-CSF) production by human retinal pigment epithelial cells. Clin Exp Immunol 1999; 115:288-293.*
Danis et al. Effects of granulocyte-macrophage colony-stimulating factor (GM-CSF), IL-2, interferon-gamma (IFN-gamma), tumour necrosis factor-alpha (TNF-alpha) and IL-6 on the production of immunoreactive IL-1 and TNF-alpha by human monocytes. Clin Exp Immunol. Jul. 1991;85(1):143-50.*
Femandez et al. Transcriptional and post-transcriptional regulation of GM-CSF-induced IL-1 beta gene expression in PMN. J. Leukoc. Biol., 1996, 59: 598-603.*
Koenders et al. IL-17 Synergy with TNF Causes Striking Cartilage Erosion In Vivo. American College of Rheumatology, 2007 Annual Scientific Meeting.*
Chabaud et al. Rheumatoid Arthritis Synoviocytes and Its and Leukemia Inhibitory Factor Production by Enhancing Effect of IL-17 on IL-1-Induced IL-6 Regulation by Th2 Cytokines. J Immunol 1998; 161:409-414.*
Andoh et al. Interleukin-17 augments tumor necrosis factor-alpha-induced granulocyte and granulocyte/macrophage colony-stimulating factor release from human colonic myofibroblasts. J Gastroenterol. Aug. 2005;40(8):802-10.*
Shen et al. Structure-function relationships in the IL-17 receptor: implications for signal transduction and therapy. Cytokine. Feb. 2008;41(2):92-104.*
Numasaki, et al. "Interluekin-17 Promotes Angiogenesis and Tumor Growth," Blood 101 :2620-2627 (2003).
First office action (and translation) from corresponding Chinese Application No. 200980115521.9 dated Aug. 24, 2012.
McAllister et al., In vitro effector activity of *Pneumocystis murina*-specific T-cytotoxic-1 CD8+ T cells: Role of granulocyte-macrophage colony-stimulating factor, *Infect. Immun.* 73:7450-7, 2005.
Smith et al., Synergism between GM-CSF and IFNγ: Enhanced immunotherapy in mice with glioma, *Int. J. Cancer* 120: 75-80, 2006.
Yoon et al., Synergistic anti-tumor effects with co-expression of GM-CSF and IFNγ in murine tumors, *Int. J. Cancer* 77: 907-12, 1998.
Van Nieuwenhuijze et al., Synergism Between GM-CSF and IL-17 Causes Enhanced Joint Pathology Via the Production of IL-6 and IL-23, *Ann. Rheum. Dis.*, 2014, A24, 73(Suppl 1), BMJ Publishing Group Ltd, London, UK.

* cited by examiner

*Primary Examiner* — Dong Jiang
(74) *Attorney, Agent, or Firm* — Marshall, Gerstein & Borun LLP

(57) ABSTRACT

The invention relates to a method for the treatment of an inflammatory disease in a subject suffering from the inflammatory disease, the method comprising the administration to said subject of a compound neutralizing GM-CSF; and a compound neutralizing IL-17.

12 Claims, 7 Drawing Sheets

SEQUENCE LISTING

```
<160> NUMBER OF SEQ ID NOS: 60

<210> SEQ ID NO 1
<211> LENGTH: 10
<212> TYPE: PRT
<213> ORGANISM: artificial sequence
<220> FEATURE:
<223> OTHER INFORMATION: CDR-H3 7A-701

<400> SEQUENCE: 1

Ser Gly Leu Ile Ala Asn His Met Thr Pro
1               5                   10

<210> SEQ ID NO 2
<211> LENGTH: 10
<212> TYPE: PRT
<213> ORGANISM: artificial sequence
<220> FEATURE:
<223> OTHER INFORMATION: CDR-H3 7B1-502

<400> SEQUENCE: 2

Thr Thr Leu Ile Ser Val Tyr Phe Asp Tyr
1               5                   10

<210> SEQ ID NO 3
<211> LENGTH: 10
<212> TYPE: PRT
<213> ORGANISM: artificial sequence
<220> FEATURE:
<223> OTHER INFORMATION: CDR-H3 L38-A1

<400> SEQUENCE: 3

Ser Gly Leu Ile Phe Asp Tyr Trp Leu Asp
1               5                   10

<210> SEQ ID NO 4
<211> LENGTH: 10
<212> TYPE: PRT
<213> ORGANISM: artificial sequence
<220> FEATURE:
<223> OTHER INFORMATION: CDR-H3 L38-A12

<400> SEQUENCE: 4

Ser Gly Leu Ile Ile Asp Ala Leu Ser Pro
```

```
1               5                  10
```

<210> SEQ ID NO 5
<211> LENGTH: 10
<212> TYPE: PRT
<213> ORGANISM: artificial sequence
<220> FEATURE:
<223> OTHER INFORMATION: CDR-H3 L38-G7

<400> SEQUENCE: 5

```
Thr Ser Leu Met Ser Ile Tyr Phe Asp Tyr
1               5                  10
```

<210> SEQ ID NO 6
<211> LENGTH: 10
<212> TYPE: PRT
<213> ORGANISM: artificial sequence
<220> FEATURE:
<223> OTHER INFORMATION: CDR-H3 L39-D11

<400> SEQUENCE: 6

```
Ser Gly Leu Leu Phe Leu Tyr Phe Asp Tyr
1               5                  10
```

<210> SEQ ID NO 7
<211> LENGTH: 10
<212> TYPE: PRT
<213> ORGANISM: artificial sequence
<220> FEATURE:
<223> OTHER INFORMATION: CDR-H3 E1-37-E7

<400> SEQUENCE: 7

```
Ser Gly Leu Ile Asn Leu Gly Met His Pro
1               5                  10
```

<210> SEQ ID NO 8
<211> LENGTH: 10
<212> TYPE: PRT
<213> ORGANISM: artificial sequence
<220> FEATURE:
<223> OTHER INFORMATION: CDR-H3 M1_3-82

<400> SEQUENCE: 8

```
Ser Gly Leu Ile Phe Asp Ala Leu Arg Asp
1               5                  10
```

<210> SEQ ID NO 9
<211> LENGTH: 10
<212> TYPE: PRT
<213> ORGANISM: artificial sequence
<220> FEATURE:
<223> OTHER INFORMATION: CDR-H3 Ln4p-23

<400> SEQUENCE: 9

```
Ser Gly Leu Ile Phe Asp Lys Leu Thr Ser
1               5                  10
```

<210> SEQ ID NO 10
<211> LENGTH: 10
<212> TYPE: PRT
<213> ORGANISM: artificial sequence
<220> FEATURE:
<223> OTHER INFORMATION: CDR-H3 Ln4p-28

<400> SEQUENCE: 10

```
Ser Gly Leu Ile Asn Leu His Phe Asp Thr
1               5                  10
```

```
<210> SEQ ID NO 11
<211> LENGTH: 10
<212> TYPE: PRT
<213> ORGANISM: artificial sequence
<220> FEATURE:
<223> OTHER INFORMATION: CDR-H3 Ln4p-50

<400> SEQUENCE: 11

Ser Thr His Phe Ser Ala Tyr Phe Asp Tyr
1               5                   10

<210> SEQ ID NO 12
<211> LENGTH: 10
<212> TYPE: PRT
<213> ORGANISM: artificial sequence
<220> FEATURE:
<223> OTHER INFORMATION: CDR-H3 Ln4p-65

<400> SEQUENCE: 12

Ser Gly Leu Ile Met Asp Lys Leu Asp Asn
1               5                   10

<210> SEQ ID NO 13
<211> LENGTH: 10
<212> TYPE: PRT
<213> ORGANISM: artificial sequence
<220> FEATURE:
<223> OTHER INFORMATION: CDR-H3 Ln4p-90

<400> SEQUENCE: 13

Ser Gly Leu Ile Ile Asp Asn Leu Asn Pro
1               5                   10

<210> SEQ ID NO 14
<211> LENGTH: 5
<212> TYPE: PRT
<213> ORGANISM: artificial sequence
<220> FEATURE:
<223> OTHER INFORMATION: CDR-H1 7B1-502

<400> SEQUENCE: 14

Asp Tyr Leu Leu His
1               5

<210> SEQ ID NO 15
<211> LENGTH: 17
<212> TYPE: PRT
<213> ORGANISM: artificial sequence
<220> FEATURE:
<223> OTHER INFORMATION: CDR-H2 7B1-502

<400> SEQUENCE: 15

Trp Leu Asn Pro Tyr Ser Gly Asp Thr Asn Tyr Ala Gln Lys Phe Gln
1               5                   10                  15

Gly

<210> SEQ ID NO 16
<211> LENGTH: 11
<212> TYPE: PRT
<213> ORGANISM: artificial sequence
<220> FEATURE:
<223> OTHER INFORMATION: CDR-L1 5-306

<400> SEQUENCE: 16

Arg Ala Ser Gln Asn Ile Arg Asn Ile Leu Asn
```

<210> SEQ ID NO 17
<211> LENGTH: 7
<212> TYPE: PRT
<213> ORGANISM: artificial sequence
<220> FEATURE:
<223> OTHER INFORMATION: CDR-L2 5-306

<400> SEQUENCE: 17

Ala Ala Ser Asn Leu Gln Ser
1               5

<210> SEQ ID NO 18
<211> LENGTH: 9
<212> TYPE: PRT
<213> ORGANISM: artificial sequence
<220> FEATURE:
<223> OTHER INFORMATION: CDR-L3 5-306

<400> SEQUENCE: 18

Gln Gln Ser Tyr Ser Met Pro Arg Thr
1               5

<210> SEQ ID NO 19
<211> LENGTH: 107
<212> TYPE: PRT
<213> ORGANISM: artificial sequence
<220> FEATURE:
<223> OTHER INFORMATION: VL 5-306* L-version

<400> SEQUENCE: 19

Asp Ile Gln Met Thr Gln Ser Pro Ser Ser Val Ser Ala Ser Val Gly
1               5                   10                  15

Asp Arg Val Thr Ile Ala Cys Arg Ala Ser Gln Asn Ile Arg Asn Ile
            20                  25                  30

Leu Asn Trp Tyr Gln Gln Arg Pro Gly Lys Ala Pro Gln Leu Leu Ile
        35                  40                  45

Tyr Ala Ala Ser Asn Leu Gln Ser Gly Val Pro Ser Arg Phe Ser Gly
    50                  55                  60

Ser Gly Ser Gly Thr Asp Phe Thr Leu Thr Ile Asn Ser Leu Gln Pro
65                  70                  75                  80

Glu Asp Phe Ala Thr Tyr Tyr Cys Gln Gln Ser Tyr Ser Met Pro Arg
                85                  90                  95

Thr Phe Gly Gly Gly Thr Lys Leu Glu Ile Lys
            100                 105

<210> SEQ ID NO 20
<211> LENGTH: 119
<212> TYPE: PRT
<213> ORGANISM: artificial sequence
<220> FEATURE:
<223> OTHER INFORMATION: VH with CDR-H3 = 7A-701

<400> SEQUENCE: 20

Glu Val Gln Leu Leu Glu Ser Gly Ala Glu Val Lys Lys Pro Gly Ala
1               5                   10                  15

Ser Val Lys Val Ser Cys Lys Ala Phe Gly Tyr Pro Phe Thr Asp Tyr
            20                  25                  30

Leu Leu His Trp Val Arg Gln Ala Pro Gly Gln Gly Leu Glu Trp Val
        35                  40                  45

Gly Trp Leu Asn Pro Tyr Ser Gly Asp Thr Asn Tyr Ala Gln Lys Phe

```
                50              55              60
Gln Gly Arg Val Thr Met Thr Arg Asp Thr Ser Ile Ser Thr Ala Tyr
 65                  70                  75                  80

Met Glu Leu Ser Arg Leu Arg Ser Asp Asp Thr Ala Val Tyr Tyr Cys
                 85                  90                  95

Thr Arg Ser Gly Leu Ile Ala Asn His Met Thr Pro Trp Gly Gln Gly
                100                 105                 110

Thr Met Val Thr Val Ser Ser
            115

<210> SEQ ID NO 21
<211> LENGTH: 119
<212> TYPE: PRT
<213> ORGANISM: artificial sequence
<220> FEATURE:
<223> OTHER INFORMATION: VH with CDR-H3 = 7B1-502*

<400> SEQUENCE: 21

Gln Val Gln Leu Val Gln Ser Gly Ala Glu Val Lys Lys Pro Gly Ala
 1               5                  10                  15

Ser Val Lys Val Ser Cys Lys Ala Phe Gly Tyr Pro Phe Thr Asp Tyr
                 20                  25                  30

Leu Leu His Trp Val Arg Gln Ala Pro Gly Gln Gly Leu Glu Trp Val
             35                  40                  45

Gly Trp Leu Asn Pro Tyr Ser Gly Asp Thr Asn Tyr Ala Gln Lys Phe
         50                  55                  60

Gln Gly Arg Val Thr Met Thr Arg Asp Thr Ser Ile Ser Thr Ala Tyr
 65                  70                  75                  80

Met Glu Leu Ser Arg Leu Arg Ser Asp Asp Thr Ala Val Tyr Tyr Cys
                 85                  90                  95

Thr Arg Thr Thr Leu Ile Ser Val Tyr Phe Asp Tyr Trp Gly Gln Gly
                100                 105                 110

Thr Met Val Thr Val Ser Ser
            115

<210> SEQ ID NO 22
<211> LENGTH: 119
<212> TYPE: PRT
<213> ORGANISM: artificial sequence
<220> FEATURE:
<223> OTHER INFORMATION: VH with CDR-H3 = 3077*

<400> SEQUENCE: 22

Gln Val Gln Leu Val Gln Ser Gly Ala Glu Val Lys Lys Pro Gly Ala
 1               5                  10                  15

Ser Val Lys Val Ser Cys Lys Ala Phe Gly Tyr Pro Phe Thr Asp Tyr
                 20                  25                  30

Leu Leu His Trp Val Arg Gln Ala Pro Gly Gln Gly Leu Glu Trp Val
             35                  40                  45

Gly Trp Leu Asn Pro Tyr Ser Gly Asp Thr Asn Tyr Ala Gln Lys Phe
         50                  55                  60

Gln Gly Arg Val Thr Met Thr Arg Asp Thr Ser Ile Ser Thr Ala Tyr
 65                  70                  75                  80

Met Glu Leu Ser Arg Leu Arg Ser Asp Asp Thr Ala Val Tyr Tyr Cys
                 85                  90                  95

Thr Arg Ser Gly Leu Ile Ala Val Tyr Phe Asp Tyr Trp Gly Gln Gly
                100                 105                 110
```

```
Thr Met Val Thr Val Ser Ser
        115

<210> SEQ ID NO 23
<211> LENGTH: 119
<212> TYPE: PRT
<213> ORGANISM: artificial sequence
<220> FEATURE:
<223> OTHER INFORMATION: VH with CDR-H3 = L38-A1

<400> SEQUENCE: 23

Glu Val Gln Leu Leu Glu Ser Gly Ala Glu Val Lys Lys Pro Gly Ala
1               5                   10                  15

Ser Val Lys Val Ser Cys Lys Ala Phe Gly Tyr Pro Phe Thr Asp Tyr
                20                  25                  30

Leu Leu His Trp Val Arg Gln Ala Pro Gly Gln Gly Leu Glu Trp Val
            35                  40                  45

Gly Trp Leu Asn Pro Tyr Ser Gly Asp Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Ser Gly Leu Ile Phe Asp Tyr Trp Leu Asp Trp Gly Gln Gly
                100                 105                 110

Thr Met Val Thr Val Ser Ser
        115

<210> SEQ ID NO 24
<211> LENGTH: 119
<212> TYPE: PRT
<213> ORGANISM: artificial sequence
<220> FEATURE:
<223> OTHER INFORMATION: VH with CDR-H3 = L38-A12

<400> SEQUENCE: 24

Glu Val Gln Leu Leu Glu Ser Gly Ala Glu Val Lys Lys Pro Gly Ala
1               5                   10                  15

Ser Val Lys Val Ser Cys Lys Ala Phe Gly Tyr Pro Phe Thr Asp Tyr
                20                  25                  30

Leu Leu His Trp Val Arg Gln Ala Pro Gly Gln Gly Leu Glu Trp Val
            35                  40                  45

Gly Trp Leu Asn Pro Tyr Ser Gly Asp Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Ser Gly Leu Ile Ile Asp Ala Leu Ser Pro Trp Gly Gln Gly
                100                 105                 110

Thr Met Val Thr Val Ser Ser
        115

<210> SEQ ID NO 25
<211> LENGTH: 119
<212> TYPE: PRT
<213> ORGANISM: artificial sequence
<220> FEATURE:
<223> OTHER INFORMATION: VH with CDR-H3 = L38-G7
```

<400> SEQUENCE: 25

Glu Val Gln Leu Leu Glu Ser Gly Ala Glu Val Lys Lys Pro Gly Ala
1               5                   10                  15

Ser Val Lys Val Ser Cys Lys Ala Phe Gly Tyr Pro Phe Thr Asp Tyr
            20                  25                  30

Leu Leu His Trp Val Arg Gln Ala Pro Gly Gln Gly Leu Glu Trp Val
        35                  40                  45

Gly Trp Leu Asn Pro Tyr Ser Gly Asp Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Thr Arg Thr Ser Leu Met Ser Ile Tyr Phe Asp Tyr Trp Gly Gln Gly
            100                 105                 110

Thr Met Val Thr Val Ser Ser
        115

<210> SEQ ID NO 26
<211> LENGTH: 119
<212> TYPE: PRT
<213> ORGANISM: artificial sequence
<220> FEATURE:
<223> OTHER INFORMATION: VH with CDR-H3 = L39-D11

<400> SEQUENCE: 26

Glu Val Gln Leu Leu Glu Ser Gly Ala Glu Val Lys Lys Pro Gly Ala
1               5                   10                  15

Ser Val Lys Val Ser Cys Lys Ala Phe Gly Tyr Pro Phe Thr Asp Tyr
            20                  25                  30

Leu Leu His Trp Val Arg Gln Ala Pro Gly Gln Gly Leu Glu Trp Val
        35                  40                  45

Gly Trp Leu Asn Pro Tyr Ser Gly Asp Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Thr Arg Ser Gly Leu Leu Phe Leu Tyr Phe Asp Tyr Trp Gly Gln Gly
            100                 105                 110

Thr Met Val Thr Val Ser Ser
        115

<210> SEQ ID NO 27
<211> LENGTH: 119
<212> TYPE: PRT
<213> ORGANISM: artificial sequence
<220> FEATURE:
<223> OTHER INFORMATION: VH with CDR-H3 = E1-37-E7

<400> SEQUENCE: 27

Glu Val Gln Leu Leu Glu Ser Gly Ala Glu Val Lys Lys Pro Gly Ala
1               5                   10                  15

Ser Val Lys Val Ser Cys Lys Ala Phe Gly Tyr Pro Phe Thr Asp Tyr
            20                  25                  30

Leu Leu His Trp Val Arg Gln Ala Pro Gly Gln Gly Leu Glu Trp Val
        35                  40                  45

Gly Trp Leu Asn Pro Tyr Ser Gly Asp Thr Asn Tyr Ala Gln Lys Phe
                50                  55                  60

Gln Gly Arg Val Thr Met Thr Arg Asp Thr Ser Ile Ser Thr Ala Tyr
 65                  70                  75                  80

Met Glu Leu Ser Arg Leu Arg Ser Asp Asp Thr Ala Val Tyr Tyr Cys
                    85                  90                  95

Ala Arg Ser Gly Leu Ile Asn Leu Gly Met His Pro Trp Gly Gln Gly
                100                 105                 110

Thr Met Val Thr Val Ser Ser
            115

<210> SEQ ID NO 28
<211> LENGTH: 119
<212> TYPE: PRT
<213> ORGANISM: artificial sequence
<220> FEATURE:
<223> OTHER INFORMATION: VH with CDR-H3 = M1_3-82

<400> SEQUENCE: 28

Glu Val Gln Leu Leu Glu Ser Gly Ala Glu Val Lys Lys Pro Gly Ala
 1               5                  10                  15

Ser Val Lys Val Ser Cys Lys Ala Phe Gly Tyr Pro Phe Thr Asp Tyr
                20                  25                  30

Leu Leu His Trp Val Arg Gln Ala Pro Gly Gln Gly Leu Glu Trp Val
            35                  40                  45

Gly Trp Leu Asn Pro Tyr Ser Gly Asp Thr Asn Tyr Ala Gln Lys Phe
        50                  55                  60

Gln Gly Arg Val Thr Met Thr Arg Asp Thr Ser Ile Ser Thr Ala Tyr
 65                  70                  75                  80

Met Glu Leu Ser Arg Leu Arg Ser Asp Asp Thr Ala Val Tyr Tyr Cys
                    85                  90                  95

Ala Arg Ser Gly Leu Ile Phe Asp Ala Leu Arg Asp Trp Gly Gln Gly
                100                 105                 110

Thr Met Val Thr Val Ser Ser
            115

<210> SEQ ID NO 29
<211> LENGTH: 119
<212> TYPE: PRT
<213> ORGANISM: artificial sequence
<220> FEATURE:
<223> OTHER INFORMATION: VH with CDR-H3 = Ln4p-23

<400> SEQUENCE: 29

Glu Val Gln Leu Leu Glu Ser Gly Ala Glu Val Lys Lys Pro Gly Ala
 1               5                  10                  15

Ser Val Lys Val Ser Cys Lys Ala Phe Gly Tyr Pro Phe Thr Asp Tyr
                20                  25                  30

Leu Leu His Trp Val Arg Gln Ala Pro Gly Gln Gly Leu Glu Trp Val
            35                  40                  45

Gly Trp Leu Asn Pro Tyr Ser Gly Asp Thr Asn Tyr Ala Gln Lys Phe
        50                  55                  60

Gln Gly Arg Val Thr Met Thr Arg Asp Thr Ser Ile Ser Thr Ala Tyr
 65                  70                  75                  80

Met Glu Leu Ser Arg Leu Arg Ser Asp Asp Thr Ala Val Tyr Tyr Cys
                    85                  90                  95

Ala Arg Ser Gly Leu Ile Phe Asp Lys Leu Thr Ser Trp Gly Gln Gly
                100                 105                 110

-continued

Thr Met Val Thr Val Ser Ser
        115

<210> SEQ ID NO 30
<211> LENGTH: 119
<212> TYPE: PRT
<213> ORGANISM: artificial sequence
<220> FEATURE:
<223> OTHER INFORMATION: VH with CDR-H3 = Ln4p-28

<400> SEQUENCE: 30

Glu Val Gln Leu Leu Glu Ser Gly Ala Glu Val Lys Lys Pro Gly Ala
1               5                   10                  15

Ser Val Lys Val Ser Cys Lys Ala Phe Gly Tyr Pro Phe Thr Asp Tyr
            20                  25                  30

Leu Leu His Trp Val Arg Gln Ala Pro Gly Gln Gly Leu Glu Trp Val
        35                  40                  45

Gly Trp Leu Asn Pro Tyr Ser Gly Asp Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Ser Gly Leu Ile Asn Leu His Phe Asp Thr Trp Gly Gln Gly
            100                 105                 110

Thr Met Val Thr Val Ser Ser
        115

<210> SEQ ID NO 31
<211> LENGTH: 119
<212> TYPE: PRT
<213> ORGANISM: artificial sequence
<220> FEATURE:
<223> OTHER INFORMATION: VH with CDR-H3 = Ln4p-50

<400> SEQUENCE: 31

Glu Val Gln Leu Leu Glu Ser Gly Ala Glu Val Lys Lys Pro Gly Ala
1               5                   10                  15

Ser Val Lys Val Ser Cys Lys Ala Phe Gly Tyr Pro Phe Thr Asp Tyr
            20                  25                  30

Leu Leu His Trp Val Arg Gln Ala Pro Gly Gln Gly Leu Glu Trp Val
        35                  40                  45

Gly Trp Leu Asn Pro Tyr Ser Gly Asp Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Thr Arg Ser Thr His Phe Ser Ala Tyr Phe Asp Tyr Trp Gly Gln Gly
            100                 105                 110

Thr Met Val Thr Val Ser Ser
        115

<210> SEQ ID NO 32
<211> LENGTH: 119
<212> TYPE: PRT
<213> ORGANISM: artificial sequence
<220> FEATURE:
<223> OTHER INFORMATION: VH with CDR-H3 = Ln4p-65

<400> SEQUENCE: 32

Glu Val Gln Leu Leu Glu Ser Gly Ala Glu Val Lys Lys Pro Gly Ala
1               5                   10                  15

Ser Val Lys Val Ser Cys Lys Ala Phe Gly Tyr Pro Phe Thr Asp Tyr
            20                  25                  30

Leu Leu His Trp Val Arg Gln Ala Pro Gly Gln Gly Leu Glu Trp Val
        35                  40                  45

Gly Trp Leu Asn Pro Tyr Ser Gly Asp Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Ser Gly Leu Ile Met Asp Lys Leu Asp Asn Trp Gly Gln Gly
                100                 105                 110

Thr Met Val Thr Val Ser Ser
        115

<210> SEQ ID NO 33
<211> LENGTH: 119
<212> TYPE: PRT
<213> ORGANISM: artificial sequence
<220> FEATURE:
<223> OTHER INFORMATION: VH with CDR-H3 = Ln4p-90

<400> SEQUENCE: 33

Glu Val Gln Leu Leu Glu Ser Gly Ala Glu Val Lys Lys Pro Gly Ala
1               5                   10                  15

Ser Val Lys Val Ser Cys Lys Ala Phe Gly Tyr Pro Phe Thr Asp Tyr
            20                  25                  30

Leu Leu His Trp Val Arg Gln Ala Pro Gly Gln Gly Leu Glu Trp Val
        35                  40                  45

Gly Trp Leu Asn Pro Tyr Ser Gly Asp Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Ser Gly Leu Ile Ile Asp Asn Leu Asn Pro Trp Gly Gln Gly
                100                 105                 110

Thr Met Val Thr Val Ser Ser
        115

<210> SEQ ID NO 34
<211> LENGTH: 214
<212> TYPE: PRT
<213> ORGANISM: artificial sequence
<220> FEATURE:
<223> OTHER INFORMATION: Light Chain 5-306* L-version

<400> SEQUENCE: 34

Asp Ile Gln Met Thr Gln Ser Pro Ser Ser Val Ser Ala Ser Val Gly
1               5                   10                  15

Asp Arg Val Thr Ile Ala Cys Arg Ala Ser Gln Asn Ile Arg Asn Ile
            20                  25                  30

Leu Asn Trp Tyr Gln Gln Arg Pro Gly Lys Ala Pro Gln Leu Leu Ile
        35                  40                  45

```
Tyr Ala Ala Ser Asn Leu Gln Ser Gly Val Pro Ser Arg Phe Ser Gly
        50                  55                  60

Ser Gly Ser Gly Thr Asp Phe Thr Leu Thr Ile Asn Ser Leu Gln Pro
 65                  70                  75                  80

Glu Asp Phe Ala Thr Tyr Tyr Cys Gln Gln Ser Tyr Ser Met Pro Arg
                     85                  90                  95

Thr Phe Gly Gly Gly Thr Lys Leu Glu Ile Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
                195                 200                 205

Phe Asn Arg Gly Glu Cys
    210

<210> SEQ ID NO 35
<211> LENGTH: 449
<212> TYPE: PRT
<213> ORGANISM: artificial sequence
<220> FEATURE:
<223> OTHER INFORMATION: Heavy Chain with CDR-H3 = 7B1-502*

<400> SEQUENCE: 35

Gln Val Gln Leu Val Gln Ser Gly Ala Glu Val Lys Lys Pro Gly Ala
 1               5                  10                  15

Ser Val Lys Val Ser Cys Lys Ala Phe Gly Tyr Pro Phe Thr Asp Tyr
                20                  25                  30

Leu Leu His Trp Val Arg Gln Ala Pro Gly Gln Gly Leu Glu Trp Val
            35                  40                  45

Gly Trp Leu Asn Pro Tyr Ser Gly Asp Thr Asn Tyr Ala Gln Lys Phe
 50                  55                  60

Gln Gly Arg Val Thr Met Thr Arg Asp Thr Ser Ile Ser Thr Ala Tyr
 65                  70                  75                  80

Met Glu Leu Ser Arg Leu Arg Ser Asp Thr Ala Val Tyr Tyr Cys
                85                  90                  95

Thr Arg Thr Thr Leu Ile Ser Val Tyr Phe Asp Tyr Trp Gly Gln Gly
                100                 105                 110

Thr Met Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
                180                 185                 190
```

```
Ser Ser Leu Gly Thr Gln Thr Tyr Ile Cys Asn Val Asn His Lys Pro
        195                 200                 205

Ser Asn Thr Lys Val Asp Lys Val Glu Pro Lys Ser Cys Asp Lys
    210                 215                 220

Thr His Thr Cys Pro Pro Cys Pro Ala Pro Glu Leu Leu Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 36
<211> LENGTH: 449
<212> TYPE: PRT
<213> ORGANISM: artificial sequence
<220> FEATURE:
<223> OTHER INFORMATION: Heavy Chain with CDR-H3 =7A-701*

<400> SEQUENCE: 36

Gln Val Gln Leu Val Gln Ser Gly Ala Glu Val Lys Lys Pro Gly Ala
1               5                   10                  15

Ser Val Lys Val Ser Cys Lys Ala Phe Gly Tyr Pro Phe Thr Asp Tyr
            20                  25                  30

Leu Leu His Trp Val Arg Gln Ala Pro Gly Gln Gly Leu Glu Trp Val
        35                  40                  45

Gly Trp Leu Asn Pro Tyr Ser Gly Asp Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95
```

```
Thr Arg Ser Gly Leu Ile Ala Asn His Met Thr Pro Trp Gly Gln Gly
            100                 105                 110

Thr Met Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 37
<211> LENGTH: 449
<212> TYPE: PRT
<213> ORGANISM: artificial sequence
<220> FEATURE:
<223> OTHER INFORMATION: Heavy Chain with CDR-H3 = L38-A1*

<400> SEQUENCE: 37

Gln Val Gln Leu Val Gln Ser Gly Ala Glu Val Lys Lys Pro Gly Ala
```

-continued

```
1               5                    10                      15
Ser Val Lys Val Ser Cys Lys Ala Phe Gly Tyr Pro Phe Thr Asp Tyr
                20                  25                  30

Leu Leu His Trp Val Arg Gln Ala Pro Gly Gln Gly Leu Glu Trp Val
            35                  40                  45

Gly Trp Leu Asn Pro Tyr Ser Gly Asp Thr Asn Tyr Ala Gln Lys Phe
        50                  55                  60

Gln Gly Arg Val Thr Met Thr Arg Asp Thr Ser Ile Ser Thr Ala Tyr
 65                 70                  75                  80

Met Glu Leu Ser Arg Leu Arg Ser Asp Thr Ala Val Tyr Tyr Cys
                85                  90                  95

Ala Arg Ser Gly Leu Ile Phe Asp Tyr Trp Leu Asp Trp Gly Gln Gly
                100                 105                 110

Thr Met Val Thr Val Ser Ser Ala Ser Thr Lys Gly Pro Ser Val Phe
                115                 120                 125

Pro Leu Ala Pro Ser Ser Lys Ser Thr Ser Gly Gly Thr Ala Ala Leu
        130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
                180                 185                 190

Ser Ser Leu Gly Thr Gln Thr Tyr Ile Cys Asn Val Asn His Lys Pro
            195                 200                 205

Ser Asn Thr Lys Val Asp Lys Lys Val Glu Pro Lys Ser Cys Asp Lys
210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
                260                 265                 270

Pro Glu Val Lys Phe Asn Trp Tyr Val Asp Gly Val Glu Val His Asn
                275                 280                 285

Ala Lys Thr Lys Pro Arg Glu Glu Gln Tyr Asn Ser Thr Tyr Arg Val
                290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
                340                 345                 350

Leu Pro Pro Ser Arg Asp Glu Leu Thr Lys Asn Gln Val Ser Leu Thr
            355                 360                 365

Cys Leu Val Lys Gly Phe Tyr Pro Ser Asp Ile Ala Val Glu Trp Glu
        370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430
```

Ala Leu His Asn His Tyr Thr Gln Lys Ser Leu Ser Leu Ser Pro Gly
            435                 440                 445

Lys

<210> SEQ ID NO 38
<211> LENGTH: 449
<212> TYPE: PRT
<213> ORGANISM: artificial sequence
<220> FEATURE:
<223> OTHER INFORMATION: Heavy Chain with CDR-H3 = L38-A12*

<400> SEQUENCE: 38

Gln Val Gln Leu Val Gln Ser Gly Ala Glu Val Lys Lys Pro Gly Ala
1               5                   10                  15

Ser Val Lys Val Ser Cys Lys Ala Phe Gly Tyr Pro Phe Thr Asp Tyr
            20                  25                  30

Leu Leu His Trp Val Arg Gln Ala Pro Gly Gln Gly Leu Glu Trp Val
        35                  40                  45

Gly Trp Leu Asn Pro Tyr Ser Gly Asp Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Ser Gly Leu Ile Ile Asp Ala Leu Ser Pro Trp Gly Gln Gly
            100                 105                 110

Thr Met Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

```
Thr Ile Ser Lys Ala Lys Gly Gln Pro Arg Glu Pro Gln Val Tyr Thr
                335                 340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
        420                 425                 430

Ala Leu His Asn His Tyr Thr Gln Lys Ser Leu Ser Leu Ser Pro Gly
                435                 440                 445

Lys

<210> SEQ ID NO 39
<211> LENGTH: 449
<212> TYPE: PRT
<213> ORGANISM: artificial sequence
<220> FEATURE:
<223> OTHER INFORMATION: Heavy Chain with CDR-H3 = L38-G7*

<400> SEQUENCE: 39

Gln Val Gln Leu Val Gln Ser Gly Ala Glu Val Lys Lys Pro Gly Ala
1               5                   10                  15

Ser Val Lys Val Ser Cys Lys Ala Phe Gly Tyr Pro Phe Thr Asp Tyr
            20                  25                  30

Leu Leu His Trp Val Arg Gln Ala Pro Gly Gln Gly Leu Glu Trp Val
        35                  40                  45

Gly Trp Leu Asn Pro Tyr Ser Gly Asp Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Thr Arg Thr Ser Leu Met Ser Ile Tyr Phe Asp Tyr Trp Gly Gln Gly
            100                 105                 110

Thr Met Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
```

```
            245                 250                 255
Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
            290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
                340                 345                 350

Leu Pro Pro Ser Arg Asp Glu Leu Thr Lys Asn Gln Val Ser Leu Thr
                355                 360                 365

Cys Leu Val Lys Gly Phe Tyr Pro Ser Asp Ile Ala Val Glu Trp Glu
                370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
                420                 425                 430

Ala Leu His Asn His Tyr Thr Gln Lys Ser Leu Ser Leu Ser Pro Gly
                435                 440                 445

Lys

<210> SEQ ID NO 40
<211> LENGTH: 449
<212> TYPE: PRT
<213> ORGANISM: artificial sequence
<220> FEATURE:
<223> OTHER INFORMATION: Heavy Chain with CDR-H3 = L39-D11*

<400> SEQUENCE: 40

Gln Val Gln Leu Val Gln Ser Gly Ala Glu Val Lys Lys Pro Gly Ala
1               5                   10                  15

Ser Val Lys Val Ser Cys Lys Ala Phe Gly Tyr Pro Phe Thr Asp Tyr
                20                  25                  30

Leu Leu His Trp Val Arg Gln Ala Pro Gly Gln Gly Leu Glu Trp Val
            35                  40                  45

Gly Trp Leu Asn Pro Tyr Ser Gly Asp Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Thr Arg Ser Gly Leu Leu Phe Leu Tyr Phe Asp Tyr Trp Gly Gln Gly
                100                 105                 110

Thr Met Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160
```

```
Asn Ser Gly Ala Leu Thr Ser Gly Val His Thr Phe Pro Ala Val Leu
            165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
            195                 200                 205

Ser Asn Thr Lys Val Asp Lys Lys Val Glu Pro Lys Ser Cys Asp Lys
            210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
            245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
            290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
            325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
            355                 360                 365

Cys Leu Val Lys Gly Phe Tyr Pro Ser Asp Ile Ala Val Glu Trp Glu
            370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
            405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
            435                 440                 445

Lys

<210> SEQ ID NO 41
<211> LENGTH: 449
<212> TYPE: PRT
<213> ORGANISM: artificial sequence
<220> FEATURE:
<223> OTHER INFORMATION: Heavy Chain with CDR-H3 = E1-37-E7*

<400> SEQUENCE: 41

Gln Val Gln Leu Val Gln Ser Gly Ala Glu Val Lys Lys Pro Gly Ala
1               5                   10                  15

Ser Val Lys Val Ser Cys Lys Ala Phe Gly Tyr Pro Phe Thr Asp Tyr
            20                  25                  30

Leu Leu His Trp Val Arg Gln Ala Pro Gly Gln Gly Leu Glu Trp Val
        35                  40                  45

Gly Trp Leu Asn Pro Tyr Ser Gly Asp Thr Asn Tyr Ala Gln Lys Phe
    50                  55                  60
```

```
Gln Gly Arg Val Thr Met Thr Arg Asp Thr Ser Ile Ser Thr Ala Tyr
 65                  70                  75                  80

Met Glu Leu Ser Arg Leu Arg Ser Asp Asp Thr Ala Val Tyr Tyr Cys
             85                  90                  95

Ala Arg Ser Gly Leu Ile Asn Leu Gly Met His Pro Trp Gly Gln Gly
            100                 105                 110

Thr Met Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 42
<211> LENGTH: 449
<212> TYPE: PRT
<213> ORGANISM: artificial sequence
```

<220> FEATURE:
<223> OTHER INFORMATION: Heavy Chain with CDR-H3 = M1_3-82*

<400> SEQUENCE: 42

```
Gln Val Gln Leu Val Gln Ser Gly Ala Glu Val Lys Lys Pro Gly Ala
1               5                   10                  15

Ser Val Lys Val Ser Cys Lys Ala Phe Gly Tyr Pro Phe Thr Asp Tyr
            20                  25                  30

Leu Leu His Trp Val Arg Gln Ala Pro Gly Gln Gly Leu Glu Trp Val
        35                  40                  45

Gly Trp Leu Asn Pro Tyr Ser Gly Asp Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Ser Gly Leu Ile Phe Asp Ala Leu Arg Asp Trp Gly Gln Gly
            100                 105                 110

Thr Met Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400
```

```
Asp Ser Asp Gly Ser Phe Phe Leu Tyr Ser Lys Leu Thr Val Asp Lys
            405                 410                 415

Ser Arg Trp Gln Gln Gly Asn Val Phe Ser Cys Ser Val Met His Glu
        420                 425                 430

Ala Leu His Asn His Tyr Thr Gln Lys Ser Leu Ser Leu Ser Pro Gly
        435                 440                 445

Lys

<210> SEQ ID NO 43
<211> LENGTH: 449
<212> TYPE: PRT
<213> ORGANISM: artificial sequence
<220> FEATURE:
<223> OTHER INFORMATION: Heavy Chain with CDR-H3 = Ln4p-23*

<400> SEQUENCE: 43

Gln Val Gln Leu Val Gln Ser Gly Ala Glu Val Lys Lys Pro Gly Ala
1               5                   10                  15

Ser Val Lys Val Ser Cys Lys Ala Phe Gly Tyr Pro Phe Thr Asp Tyr
                20                  25                  30

Leu Leu His Trp Val Arg Gln Ala Pro Gly Gln Gly Leu Glu Trp Val
            35                  40                  45

Gly Trp Leu Asn Pro Tyr Ser Gly Asp Thr Asn Tyr Ala Gln Lys Phe
50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Ser Gly Leu Ile Phe Asp Lys Leu Thr Ser Trp Gly Gln Gly
            100                 105                 110

Thr Met Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300
```

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
            325                 330                 335

Thr Ile Ser Lys Ala Lys Gly Gln Pro Arg Glu Pro Gln Val Tyr Thr
        340                 345                 350

Leu Pro Pro Ser Arg Asp Glu Leu Thr Lys Asn Gln Val Ser Leu Thr
    355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
            405                 410                 415

Ser Arg Trp Gln Gln Gly Asn Val Phe Ser Cys Ser Val Met His Glu
        420                 425                 430

Ala Leu His Asn His Tyr Thr Gln Lys Ser Leu Ser Leu Ser Pro Gly
    435                 440                 445

Lys

<210> SEQ ID NO 44
<211> LENGTH: 449
<212> TYPE: PRT
<213> ORGANISM: artificial sequence
<220> FEATURE:
<223> OTHER INFORMATION: Heavy Chain with CDR-H3 = Ln4p-28*

<400> SEQUENCE: 44

Gln Val Gln Leu Val Gln Ser Gly Ala Glu Val Lys Lys Pro Gly Ala
1               5                   10                  15

Ser Val Lys Val Ser Cys Lys Ala Phe Gly Tyr Pro Phe Thr Asp Tyr
            20                  25                  30

Leu Leu His Trp Val Arg Gln Ala Pro Gly Gln Gly Leu Glu Trp Val
        35                  40                  45

Gly Trp Leu Asn Pro Tyr Ser Gly Asp Thr Asn Tyr Ala Gln Lys Phe
50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Ser Gly Leu Ile Asn Leu His Phe Asp Thr Trp Gly Gln Gly
            100                 105                 110

Thr Met Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys

```
                    210                 215                 220
Thr His Thr Cys Pro Pro Cys Pro Ala Pro Glu Leu Gly Gly Pro
225                 230                 235                 240

Ser Val Phe Leu Phe Pro Pro Lys Pro Lys Asp Thr Leu Met Ile Ser
                    245                 250                 255

Arg Thr Pro Glu Val Thr Cys Val Val Val Asp Val Ser His Glu Asp
                260                 265                 270

Pro Glu Val Lys Phe Asn Trp Tyr Val Asp Gly Val Glu Val His Asn
                275                 280                 285

Ala Lys Thr Lys Pro Arg Glu Glu Gln Tyr Asn Ser Thr Tyr Arg Val
            290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                    325                 330                 335

Thr Ile Ser Lys Ala Lys Gly Gln Pro Arg Glu Pro Gln Val Tyr Thr
                340                 345                 350

Leu Pro Pro Ser Arg Asp Glu Leu Thr Lys Asn Gln Val Ser Leu Thr
                355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
                420                 425                 430

Ala Leu His Asn His Tyr Thr Gln Lys Ser Leu Ser Leu Ser Pro Gly
                435                 440                 445

Lys

<210> SEQ ID NO 45
<211> LENGTH: 449
<212> TYPE: PRT
<213> ORGANISM: artificial sequence
<220> FEATURE:
<223> OTHER INFORMATION: Heavy Chain with CDR-H3 = Ln4p-50*

<400> SEQUENCE: 45

Gln Val Gln Leu Val Gln Ser Gly Ala Glu Val Lys Lys Pro Gly Ala
1               5                   10                  15

Ser Val Lys Val Ser Cys Lys Ala Phe Gly Tyr Pro Phe Thr Asp Tyr
                20                  25                  30

Leu Leu His Trp Val Arg Gln Ala Pro Gly Gln Gly Leu Glu Trp Val
            35                  40                  45

Gly Trp Leu Asn Pro Tyr Ser Gly Asp Thr Asn Tyr Ala Gln Lys Phe
        50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Thr Arg Ser Thr His Phe Ser Ala Tyr Phe Asp Tyr Trp Gly Gln Gly
                100                 105                 110

Thr Met Val Thr Val Ser Ser Ala Ser Thr Lys Gly Pro Ser Val Phe
            115                 120                 125
```

```
Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 46
<211> LENGTH: 449
<212> TYPE: PRT
<213> ORGANISM: artificial sequence
<220> FEATURE:
<223> OTHER INFORMATION: Heavy Chain with CDR-H3 = Ln4p-65*

<400> SEQUENCE: 46

Gln Val Gln Leu Val Gln Ser Gly Ala Glu Val Lys Lys Pro Gly Ala
1               5                   10                  15

Ser Val Lys Val Ser Cys Lys Ala Phe Gly Tyr Pro Phe Thr Asp Tyr
            20                  25                  30
```

```
Leu Leu His Trp Val Arg Gln Ala Pro Gly Gln Gly Leu Glu Trp Val
             35                  40                  45
Gly Trp Leu Asn Pro Tyr Ser Gly Asp Thr Asn Tyr Ala Gln Lys Phe
 50                  55                  60
Gln Gly Arg Val Thr Met Thr Arg Asp Thr Ser Ile Ser Thr Ala Tyr
 65                  70                  75                  80
Met Glu Leu Ser Arg Leu Arg Ser Asp Asp Thr Ala Val Tyr Tyr Cys
             85                  90                  95
Ala Arg Ser Gly Leu Ile Met Asp Lys Leu Asp Asn Trp Gly Gln Gly
                100                 105                 110
Thr Met Val Thr Val Ser Ser Ala Ser Thr Lys Gly Pro Ser Val Phe
            115                 120                 125
Pro Leu Ala Pro Ser Ser Lys Ser Thr Ser Gly Gly Thr Ala Ala Leu
130                 135                 140
Gly Cys Leu Val Lys Asp Tyr Phe Pro Glu Pro Val Thr Val Ser Trp
145                 150                 155                 160
Asn Ser Gly Ala Leu Thr Ser Gly Val His Thr Phe Pro Ala Val Leu
                165                 170                 175
Gln Ser Ser Gly Leu Tyr Ser Leu Ser Ser Val Val Thr Val Pro Ser
            180                 185                 190
Ser Ser Leu Gly Thr Gln Thr Tyr Ile Cys Asn Val Asn His Lys Pro
        195                 200                 205
Ser Asn Thr Lys Val Asp Lys Lys Val Glu Pro Lys Ser Cys Asp Lys
    210                 215                 220
Thr His Thr Cys Pro Pro Cys Pro Ala Pro Glu Leu Leu Gly Gly Pro
225                 230                 235                 240
Ser Val Phe Leu Phe Pro Pro Lys Pro Lys Asp Thr Leu Met Ile Ser
                245                 250                 255
Arg Thr Pro Glu Val Thr Cys Val Val Val Asp Val Ser His Glu Asp
            260                 265                 270
Pro Glu Val Lys Phe Asn Trp Tyr Val Asp Gly Val Glu Val His Asn
        275                 280                 285
Ala Lys Thr Lys Pro Arg Glu Glu Gln Tyr Asn Ser Thr Tyr Arg Val
    290                 295                 300
Val Ser Val Leu Thr Val Leu His Gln Asp Trp Leu Asn Gly Lys Glu
305                 310                 315                 320
Tyr Lys Cys Lys Val Ser Asn Lys Ala Leu Pro Ala Pro Ile Glu Lys
                325                 330                 335
Thr Ile Ser Lys Ala Lys Gly Gln Pro Arg Glu Pro Gln Val Tyr Thr
            340                 345                 350
Leu Pro Pro Ser Arg Asp Glu Leu Thr Lys Asn Gln Val Ser Leu Thr
        355                 360                 365
Cys Leu Val Lys Gly Phe Tyr Pro Ser Asp Ile Ala Val Glu Trp Glu
    370                 375                 380
Ser Asn Gly Gln Pro Glu Asn Asn Tyr Lys Thr Thr Pro Pro Val Leu
385                 390                 395                 400
Asp Ser Asp Gly Ser Phe Phe Leu Tyr Ser Lys Leu Thr Val Asp Lys
                405                 410                 415
Ser Arg Trp Gln Gln Gly Asn Val Phe Ser Cys Ser Val Met His Glu
            420                 425                 430
Ala Leu His Asn His Tyr Thr Gln Lys Ser Leu Ser Leu Ser Pro Gly
        435                 440                 445
Lys
```

<210> SEQ ID NO 47
<211> LENGTH: 449
<212> TYPE: PRT
<213> ORGANISM: artificial sequence
<220> FEATURE:
<223> OTHER INFORMATION: Heavy Chain with CDR-H3 = Ln4p-90*

<400> SEQUENCE: 47

```
Gln Val Gln Leu Val Gln Ser Gly Ala Glu Val Lys Lys Pro Gly Ala
1               5                   10                  15

Ser Val Lys Val Ser Cys Lys Ala Phe Gly Tyr Pro Phe Thr Asp Tyr
            20                  25                  30

Leu Leu His Trp Val Arg Gln Ala Pro Gly Gln Gly Leu Glu Trp Val
        35                  40                  45

Gly Trp Leu Asn Pro Tyr Ser Gly Asp Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Ser Gly Leu Ile Ile Asp Asn Leu Asn Pro Trp Gly Gln Gly
            100                 105                 110

Thr Met Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365
```

Cys Leu Val Lys Gly Phe Tyr Pro Ser Asp Ile Ala Val Glu Trp Glu
        370             375             380

Ser Asn Gly Gln Pro Glu Asn Asn Tyr Lys Thr Thr Pro Pro Val Leu
385             390             395             400

Asp Ser Asp Gly Ser Phe Phe Leu Tyr Ser Lys Leu Thr Val Asp Lys
            405             410             415

Ser Arg Trp Gln Gln Gly Asn Val Phe Ser Cys Ser Val Met His Glu
        420             425             430

Ala Leu His Asn His Tyr Thr Gln Lys Ser Leu Ser Leu Ser Pro Gly
        435             440             445

Lys

<210> SEQ ID NO 48
<211> LENGTH: 449
<212> TYPE: PRT
<213> ORGANISM: artificial sequence
<220> FEATURE:
<223> OTHER INFORMATION: Heavy Chain with CDR-H3 = 3077*

<400> SEQUENCE: 48

Gln Val Gln Leu Val Gln Ser Gly Ala Glu Val Lys Lys Pro Gly Ala
1               5                   10                  15

Ser Val Lys Val Ser Cys Lys Ala Phe Gly Tyr Pro Phe Thr Asp Tyr
            20                  25                  30

Leu Leu His Trp Val Arg Gln Ala Pro Gly Gln Gly Leu Glu Trp Val
        35                  40                  45

Gly Trp Leu Asn Pro Tyr Ser Gly Asp Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Thr Arg Ser Gly Leu Ile Ala Val Tyr Phe Asp Tyr Trp Gly Gln Gly
            100                 105                 110

Thr Met Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

```
Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
        290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 49
<211> LENGTH: 127
<212> TYPE: PRT
<213> ORGANISM: human GM-CSF

<400> SEQUENCE: 49

Ala Pro Ala Arg Ser Pro Ser Pro Ser Thr Gln Pro Trp Glu His Val
1               5                   10                  15

Asn Ala Ile Gln Glu Ala Arg Arg Leu Leu Asn Leu Ser Arg Asp Thr
            20                  25                  30

Ala Ala Glu Met Asn Glu Thr Val Glu Val Ile Ser Glu Met Phe Asp
        35                  40                  45

Leu Gln Glu Pro Thr Cys Leu Gln Thr Arg Leu Glu Leu Tyr Lys Gln
    50                  55                  60

Gly Leu Arg Gly Ser Leu Thr Lys Leu Lys Gly Pro Leu Thr Met Met
65                  70                  75                  80

Ala Ser His Tyr Lys Gln His Cys Pro Pro Thr Pro Glu Thr Ser Cys
                85                  90                  95

Ala Thr Gln Ile Ile Thr Phe Glu Ser Phe Lys Glu Asn Leu Lys Asp
            100                 105                 110

Phe Leu Leu Val Ile Pro Phe Asp Cys Trp Glu Pro Val Gln Glu
        115                 120                 125

<210> SEQ ID NO 50
<211> LENGTH: 127
<212> TYPE: PRT
<213> ORGANISM: macaca GM-CSF

<400> SEQUENCE: 50

Ala Pro Ala Arg Ser Pro Ser Pro Gly Thr Gln Pro Trp Glu His Val
1               5                   10                  15

Asn Ala Ile Gln Glu Ala Arg Arg Leu Leu Asn Leu Ser Arg Asp Thr
```

```
            20                  25                  30
Ala Ala Glu Met Asn Lys Thr Val Glu Val Val Ser Glu Met Phe Asp
            35                  40                  45

Leu Gln Glu Pro Ser Cys Leu Gln Thr Arg Leu Glu Leu Tyr Lys Gln
            50                  55                  60

Gly Leu Gln Gly Ser Leu Thr Lys Leu Lys Gly Pro Leu Thr Met Met
 65                 70                  75                  80

Ala Ser His Tyr Lys Gln His Cys Pro Pro Thr Pro Glu Thr Ser Cys
            85                  90                  95

Ala Thr Gln Ile Ile Thr Phe Gln Ser Phe Lys Glu Asn Leu Lys Asp
            100                 105                 110

Phe Leu Leu Val Ile Pro Phe Asp Cys Trp Glu Pro Val Gln Glu
            115                 120                 125

<210> SEQ ID NO 51
<211> LENGTH: 127
<212> TYPE: PRT
<213> ORGANISM: gibbon GM-CSF

<400> SEQUENCE: 51

Ala Pro Ser Arg Ser Pro Ser Pro Ser Thr Gln Pro Trp Glu His Val
 1               5                   10                  15

Asn Ala Ile Gln Glu Ala Arg Arg Leu Leu Asn Leu Ser Arg Asp Thr
            20                  25                  30

Ala Ala Glu Ile Asn Glu Thr Val Glu Val Val Ser Glu Met Phe Asp
            35                  40                  45

Leu Gln Glu Pro Thr Cys Leu Gln Thr Arg Leu Glu Leu Tyr Lys Gln
            50                  55                  60

Gly Leu Arg Gly Ser Leu Thr Lys Leu Lys Gly Pro Leu Thr Met Met
 65                 70                  75                  80

Ala Ser His Tyr Lys Gln His Cys Pro Pro Thr Pro Glu Thr Ser Cys
            85                  90                  95

Ala Thr Gln Ile Ile Ile Phe Glu Ser Phe Lys Glu Asn Leu Lys Asp
            100                 105                 110

Phe Leu Leu Val Ile Pro Phe Asp Cys Trp Glu Pro Val Gln Gly
            115                 120                 125

<210> SEQ ID NO 52
<211> LENGTH: 119
<212> TYPE: PRT
<213> ORGANISM: artificial sequence
<220> FEATURE:
<223> OTHER INFORMATION: VH with CDR-H3 7B1-502

<400> SEQUENCE: 52

Glu Val Gln Leu Leu Glu Ser Gly Ala Glu Val Lys Lys Pro Gly Ala
 1               5                   10                  15

Ser Val Lys Val Ser Cys Lys Ala Phe Gly Tyr Pro Phe Thr Asp Tyr
            20                  25                  30

Leu Leu His Trp Val Arg Gln Ala Pro Gly Gln Gly Leu Glu Trp Val
            35                  40                  45

Gly Trp Leu Asn Pro Tyr Ser Asp Thr Asn Tyr Ala Gln Lys Phe
            50                  55                  60

Gln Gly Arg Val Thr Met Thr Arg Asp Thr Ser Ile Ser Thr Ala Tyr
 65                 70                  75                  80

Met Glu Leu Ser Arg Leu Arg Ser Asp Asp Thr Ala Val Tyr Tyr Cys
            85                  90                  95
```

```
Thr Arg Thr Thr Leu Ile Ser Val Tyr Phe Asp Tyr Trp Gln Gly
            100                 105                 110

Thr Met Val Thr Val Ser Ser
        115
```

<210> SEQ ID NO 53
<211> LENGTH: 119
<212> TYPE: PRT
<213> ORGANISM: artificial sequence
<220> FEATURE:
<223> OTHER INFORMATION: VH with CDR-H3 3077

<400> SEQUENCE: 53

```
Glu Val Gln Leu Leu Glu Ser Gly Ala Glu Val Lys Lys Pro Gly Ala
1               5                   10                  15

Ser Val Lys Val Ser Cys Lys Ala Phe Gly Tyr Pro Phe Thr Asp Tyr
            20                  25                  30

Leu Leu His Trp Val Arg Gln Ala Pro Gly Gln Gly Leu Glu Trp Val
        35                  40                  45

Gly Trp Leu Asn Pro Tyr Ser Gly Asp Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Thr Arg Ser Gly Leu Ile Ala Val Tyr Phe Asp Tyr Trp Gln Gly
            100                 105                 110

Thr Met Val Thr Val Ser Ser
        115
```

<210> SEQ ID NO 54
<211> LENGTH: 107
<212> TYPE: PRT
<213> ORGANISM: artificial sequence
<220> FEATURE:
<223> OTHER INFORMATION: VL 5-306

<400> SEQUENCE: 54

```
Glu Leu Val Met Thr Gln Ser Pro Ser Ser Val Ser Ala Ser Val Gly
1               5                   10                  15

Asp Arg Val Thr Ile Ala Cys Arg Ala Ser Gln Asn Ile Arg Asn Ile
            20                  25                  30

Leu Asn Trp Tyr Gln Gln Arg Pro Gly Lys Ala Pro Gln Leu Leu Ile
        35                  40                  45

Tyr Ala Ala Ser Asn Leu Gln Ser Gly Val Pro Ser Arg Phe Ser Gly
    50                  55                  60

Ser Gly Ser Gly Thr Asp Phe Thr Leu Thr Ile Asn Ser Leu Gln Pro
65                  70                  75                  80

Glu Asp Phe Ala Thr Tyr Tyr Cys Gln Gln Ser Tyr Ser Met Pro Arg
                85                  90                  95

Thr Phe Gly Gly Gly Thr Lys Val Glu Ile Lys
            100                 105
```

<210> SEQ ID NO 55
<211> LENGTH: 107
<212> TYPE: PRT
<213> ORGANISM: artificial sequence
<220> FEATURE:
<223> OTHER INFORMATION: VL 5-306* V-version

<400> SEQUENCE: 55

Asp Ile Gln Met Thr Gln Ser Pro Ser Ser Val Ser Ala Ser Val Gly
1               5                   10                  15

Asp Arg Val Thr Ile Ala Cys Arg Ala Ser Gln Asn Ile Arg Asn Ile
            20                  25                  30

Leu Asn Trp Tyr Gln Gln Arg Pro Gly Lys Ala Pro Gln Leu Leu Ile
        35                  40                  45

Tyr Ala Ala Ser Asn Leu Gln Ser Gly Val Pro Ser Arg Phe Ser Gly
    50                  55                  60

Ser Gly Ser Gly Thr Asp Phe Thr Leu Thr Ile Asn Ser Leu Gln Pro
65                  70                  75                  80

Glu Asp Phe Ala Thr Tyr Tyr Cys Gln Gln Ser Tyr Ser Met Pro Arg
                85                  90                  95

Thr Phe Gly Gly Gly Thr Lys Val Glu Ile Lys
            100                 105

<210> SEQ ID NO 56
<211> LENGTH: 10
<212> TYPE: PRT
<213> ORGANISM: artificial sequence
<220> FEATURE:
<223> OTHER INFORMATION: CDR-H3 3077

<400> SEQUENCE: 56

Ser Gly Leu Ile Ala Val Tyr Phe Asp Tyr
1               5                   10

<210> SEQ ID NO 57
<211> LENGTH: 127
<212> TYPE: PRT
<213> ORGANISM: Homo sapiens

<400> SEQUENCE: 57

Ala Pro Ala Arg Ser Pro Ser Pro Ser Thr Gln Pro Trp Glu His Val
1               5                   10                  15

Asn Ala Ile Gln Glu Ala Arg Arg Leu Leu Asn Leu Ser Arg Asp Thr
            20                  25                  30

Ala Ala Glu Met Asn Glu Thr Val Glu Val Ile Ser Glu Met Phe Asp
        35                  40                  45

Leu Gln Glu Pro Thr Cys Leu Gln Thr Arg Leu Glu Leu Tyr Lys Gln
    50                  55                  60

Gly Leu Arg Gly Ser Leu Thr Lys Leu Lys Gly Pro Leu Thr Met Met
65                  70                  75                  80

Ala Ser His Tyr Lys Gln His Cys Pro Pro Thr Pro Glu Thr Ser Cys
                85                  90                  95

Ala Thr Gln Ile Ile Thr Phe Glu Ser Phe Lys Glu Asn Leu Lys Asp
            100                 105                 110

Phe Leu Leu Val Ile Pro Phe Asp Cys Trp Glu Pro Val Gln Glu
        115                 120                 125

<210> SEQ ID NO 58
<211> LENGTH: 127
<212> TYPE: PRT
<213> ORGANISM: Hylobates sp.

<400> SEQUENCE: 58

Ala Pro Ala Arg Ser Pro Ser Pro Ser Thr Gln Pro Trp Glu His Val
1               5                   10                  15

-continued

```
Asn Ala Ile Gln Glu Ala Arg Arg Leu Leu Asn Leu Ser Arg Asp Thr
            20                  25                  30

Ala Ala Glu Met Asn Glu Thr Val Glu Val Ile Ser Glu Met Phe Asp
        35                  40                  45

Leu Gln Glu Pro Thr Cys Leu Gln Thr Arg Leu Glu Leu Tyr Lys Gln
    50                  55                  60

Gly Leu Arg Gly Ser Leu Thr Lys Leu Lys Gly Pro Leu Thr Met Met
65                  70                  75                  80

Ala Ser His Tyr Lys Gln His Cys Pro Pro Thr Pro Glu Thr Ser Cys
                85                  90                  95

Ala Thr Gln Ile Ile Thr Phe Glu Ser Phe Lys Glu Asn Leu Lys Asp
            100                 105                 110

Phe Leu Leu Val Ile Pro Phe Asp Cys Trp Glu Pro Val Gln Glu
        115                 120                 125

<210> SEQ ID NO 59
<211> LENGTH: 127
<212> TYPE: PRT
<213> ORGANISM: Macaca mulatta

<400> SEQUENCE: 59

Ala Pro Ala Arg Ser Pro Ser Pro Gly Thr Gln Pro Trp Glu His Val
1               5                   10                  15

Asn Ala Ile Gln Glu Ala Arg Arg Leu Leu Asn Leu Ser Arg Asp Thr
            20                  25                  30

Ala Ala Glu Met Asn Lys Thr Val Glu Val Val Ser Glu Met Phe Asp
        35                  40                  45

Leu Gln Glu Pro Ser Cys Leu Gln Thr Arg Leu Glu Leu Tyr Lys Gln
    50                  55                  60

Gly Leu Gln Gly Ser Leu Thr Lys Leu Lys Gly Pro Leu Thr Met Met
65                  70                  75                  80

Ala Ser His Tyr Lys Gln His Cys Pro Pro Thr Pro Glu Thr Ser Cys
                85                  90                  95

Ala Thr Gln Ile Ile Thr Phe Glu Ser Phe Lys Glu Asn Leu Lys Asp
            100                 105                 110

Phe Leu Leu Val Ile Pro Phe Asp Cys Trp Glu Pro Val Gln Glu
        115                 120                 125

<210> SEQ ID NO 60
<211> LENGTH: 127
<212> TYPE: PRT
<213> ORGANISM: Macaca fascicularis

<400> SEQUENCE: 60

Ala Pro Ala Arg Ser Pro Ser Pro Gly Thr Gln Pro Trp Glu His Val
1               5                   10                  15

Asn Ala Ile Gln Glu Ala Arg Arg Leu Leu Asn Leu Ser Arg Asp Thr
            20                  25                  30

Ala Ala Glu Met Asn Lys Thr Val Glu Val Val Ser Glu Met Phe Asp
        35                  40                  45

Leu Gln Glu Pro Ser Cys Leu Gln Thr Arg Leu Glu Leu Tyr Lys Gln
    50                  55                  60

Gly Leu Gln Gly Ser Leu Thr Lys Leu Lys Gly Pro Leu Thr Met Met
65                  70                  75                  80

Ala Ser His Tyr Lys Gln His Cys Pro Pro Thr Pro Glu Thr Ser Cys
                85                  90                  95
```

```
Ala Thr Gln Ile Ile Thr Phe Gln Ser Phe Lys Glu Asn Leu Lys Asp
            100                 105                 110

Phe Leu Leu Val Ile Pro Phe Asp Cys Trp Glu Pro Val Gln Glu
        115                 120                 125
```

METHOD OF TREATMENT BY THE ADMINISTRATION OF INHIBITORS OF GM-CSF AND IL-17

Figure 1:
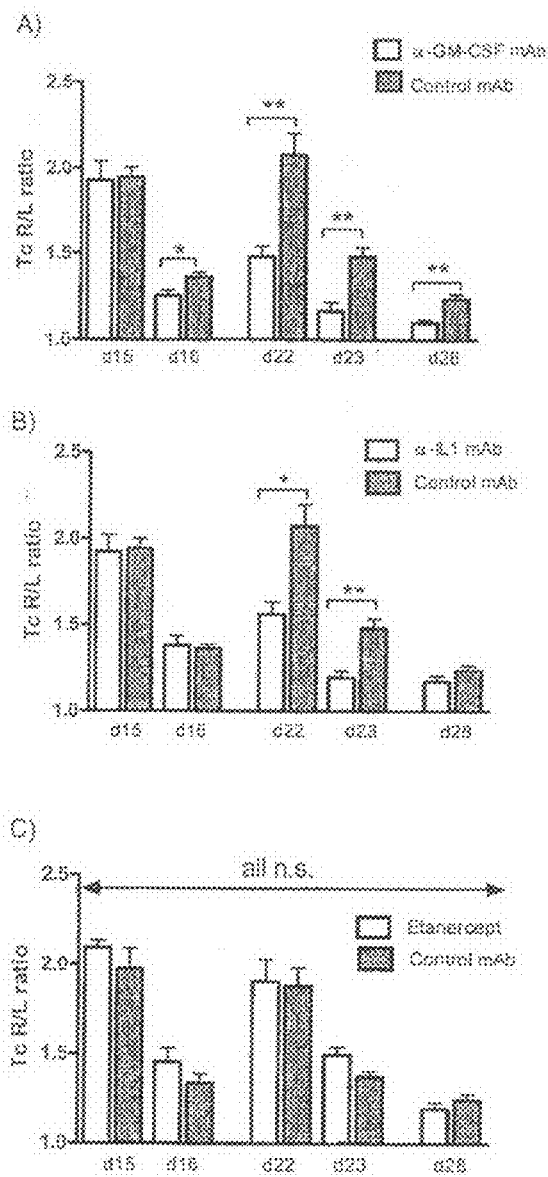

The present invention relates to the treatment of inflammatory diseases. Another aspect of the present invention relates to the treatment of tumorous diseases such as cancer. Still another aspect of the present invention relates to a pharmaceutical composition for the treatment of inflammatory and/or tumorous diseases. Depending on the jurisprudence where this application is to be filed, the invention may likewise relate to the use of two particular substances in the manufacture of a pharmaceutical for the treatment of the above diseases.

Granulocyte-macrophage colony stimulating factor (GM-CSF), initially identified as a hematopoietic growth factor, has more recently been shown to be an important cytokine in inflammation and autoimmunity. Elevated levels of GM-CSF mRNA or protein are measured in a variety of inflammatory sites including in allergic and psoriatic patients, arthritic and asthmatic patients.

Numerous in vivo studies have shown over the past few years that blockade of GM-CSF via neutralizing antibodies can prevent or even cure pro-inflammatory diseases in various models of inflammation including models for arthritis experimental autoimmune encephalitis, psoriasis, and lung disease. GM-CSF plays an important role in innate immunity by stimulating the proliferation and activation of mature neutrophils and macrophages. In addition, a key role for GM-CSF has been demonstrated in antigen-presentation by governing differentiation and maturation of dendritic cells in vitro. In vivo, GM-CSF has been reported to preferentially induce type 1 pro-inflammatory cytokines by human PBMC, T cells and APC.

Interleukin-17 (IL-17) is a family of cytokines of the acquired immune system, presently consisting of six members, IL-17A to IL-17F. IL-17 is described to bind to IL-17 receptors, a family presently comprising five members, IL-17RA to IL-17RE, which share considerable sequence homology with each other. The members of the IL-17 receptor family are type I transmembrane proteins. Presently it is generally accepted that receptors for IL-17 are abundantly expressed by all cells of the immune system, and stimulation of various cell types with IL-17A, IL-17F and IL-17D can induce the expression of other cytokines like IL-1β, TNFα and IL-6, and the chemokines IL-8 and MIP-1α. In contrast to its receptors, IL-17 is mainly produced by the recently discovered Th17 cell, and its expression has been frequently related to infection and autoimmunity.

Rheumatoid arthritis (RA) is a chronic, inflammatory, and systemic autoimmune disease. Although the aetiology and pathogenesis of RA is not yet fully understood, the disease is characterized by aggressive synovial hyperplasia (pannus formation) and inflammation (synovitis), which lead to progressive destruction of joint cartilage and bone. Rheumatoid arthritis (RA) results from complex interactions between many cell types and factors belonging to both the innate and acquired arms of the immune system. For example, it has been reported that a general increase of different cytokine expression is observed in RA patients, i.e. much higher levels of IL-2, IL-4, IL-5, IL-7, IL-10, IL-13, IFNγ, G-CSF, GM-CSF, MCP-1 and MIP-1β compared to controls. Moreover, IL-1, TNFα and IL-18 have been identified as prominent inflammatory factors stimulating T cells in RA. Published reports have hypothesized a pathogenic role for GM-CSF in RA. In support for this hypothesis are the findings (i) that GM-CSF is produced in synovium of RA patients and that elevated levels of this cytokine can be measured in their synovial fluid; (ii) that treatment with a neutralizing anti-GM-CSF monoclonal antibody (mAb) decreases disease severity in the collagen-induced mouse model for arthritis (CIA); (iii) that GM-CSF-deficient mice have a reduced susceptibility to disease induction by collagen and mBSA; (iv) that injection of recombinant GM-CSF to CIA mice exacerbates disease; and (v) that RA patients receiving GM-CSF after chemotherapy show flares of arthritis severity.

Apart from the above identified different cytokines, IL-17 also appears implicated in RA pathology because IL-17 levels are elevated in RA synovium and synovial fluid, and IL-17 blockade reduces joint inflammation and destruction during arthritis in experimental models. In addition, mice genetically deficient of IL-17 show suppressed collagen-induced arthritis, and when crossed to IL-1Ra−/− mice, IL-17−/− mice completely lack the spontaneous onset of polyarthritis usually seen in Balb/c mice deficient for the IL-1 receptor antagnoist. It has been also reported that local costimulation with IL-17 plus TNFα in mouse in vivo experiments caused a GM-CSF-dependent accumulation of neutrophils in the airways via effects on both recruitment and survival of neutrophils.

One of the models used for investigating human RA-like disease in mice is the Streptococcal cell wall (SCW) arthritis. In this model, both an acute disease and a chronic relapsing arthritis can be induced by intra-articular (i.a) injection of bacterial cell wall fragments into one knee joint of mice. An acute arthritis, in which the innate immunity plays the major pathogenic role, is obtained by a single injection of SCW fragments into knee joints of naive mice. By repeated i.a. injection of SCW fragments, a chronic relapsing model is established where mediators of acquired immunity gradually take over the initial dominance of the innate response. Collagen-induced arthritis (CIA) is another widely accepted arthritis model based on T cell and antibody-mediated autoimmune reactivity against cartilage collagen type II (CII). This mouse model shares several clinical, histopathological and immunological features with human RA, and is mainly characterized by synovial inflammation followed by severe cartilage and bone erosions. The present inventors explored the therapeutic efficacy of GM-CSF neutralization in the TNFα-independent chronic SCW arthritis model and the TNFα-dependent CIA model. In addition, they studied the effect of blocking both innate and adaptive immunity by inhibiting the GM-CSF and IL-17 pathways. This was performed by neutralizing GM-CSF in mice genetically deficient for IL-17 receptor (IL-17R-KO mice) or by combination treatment with compounds neutralizing GM-CSF and IL-17. The inventors surprisingly observed that both types of inflammatory diseases can be treated in a highly effective manner, by the combined blockade of GM-CSF and IL-17 pathways. In the CIA model, the combined administration of a GM-CSF inhibiting compound and an IL-17 inhibiting compound significantly reduced clinical scores of collagen-induced arthritis, whereas treatment with the GM-CSF inhibiting compound or the IL-17 inhibiting compound alone did not significantly decrease the severity of arthritis. In addition, a detailed histological analysis demonstrated the synergistic effect of the combination therapy on joint inflammation and destruction of cartilage and bone. Thus, the combined blockade of both pathways resulted in a highly efficient protection from inflammation and joint destruction. These results were particularly surprising as, up to very recently, it was hypothesized that GM-CSF lies downstream of IL-17 (see e.g. Kawaguchi M. et al., J. Allergy Clin. Immunol. 114 (2004), 444-450; Starnes T. et al., The Journal of Immunology 169 (2002), 642-646; Laan M. et al., Eur. Respir. J. 21 (2003), 387-393). Therefore, no additive or synergetic effect was expected from treatments combining compounds neutralizing GM-CSF and IL-17. The present application is first to demonstrate the advantageous effects of combined blocking of IL-17 and GM-CSF in vivo. The data presented here make a strong point that anti-GM-CSF in combination with anti-IL-17 treatment does not only have a profound therapeutic effect in RA but also in other autoimmune and inflammatory disease settings, as defined herein below.

Thus, the pharmaceutical means and methods of the present invention are particularly directed to the treatment of arthritis but may also apply to other inflammatory diseases including multiple sclerosis, psoriasis and lung inflammation such as asthma and chronic obstructive pulmonary disease (COPD).

DEFINITIONS

The term "subject" as used herein throughout the present text refers to an animal. The term "animal" includes, but is not limited to, mammals such as laboratory animals (rodents, e.g., rats, guinea-pigs, hamsters or mice, non-human primates, e.g., cynomolgus or macaque monkey), domestic or pet animals (e.g., dogs or cats), farm or agricultural animals (e.g., bovine, ovine, caprine, and porcine animals) and/or humans. Preferably, the animal is a human or a non-human primate.

The term "GM-CSF", as used herein throughout the present text, stands for both human (*Homo sapiens*) and non-human primate GM-CSF, as defined in the literature, and includes variants (homologs) thereof. The term also includes human and non-human primate GM-CSF receptor, and variants (homologs) thereof. Especially preferred variants (homologs) of non-human primate GM-CSF or non-human primate GM-CSF receptor include those of gibbon monkey (*nomascus concolor*, also known as the western black crested gibbon) and of monkeys of the macaca family, for example rhesus monkey (*Macaca mulatta*) and cynomolgous monkey (*Macaca fascicularis*).

The term "antibody binding to GM-CSF or to GM-CSF receptor", or a functional fragment thereof, as used herein throughout the present text, includes any antibody or antibody fragment having the capacity to bind to GM-CSF or GM-CSF receptor of an animal. In particular, it includes any antibody, or fragment thereof, exhibiting cross-reactivity (in regard of binding to GM-CSF or GM-CSF receptor) between human and at least one of the monkey species mentioned above. For example, the antibody or fragment thereof is capable of binding to (and neutralizing) both human GM-CSF and GM-CSF of the cynomolgus monkey (*Macaca fascicularis*). This is especially advantageous for an antibody molecule which is intended for therapeutic administration in human subjects, since such antibody will normally have to proceed through a multitude of tests prior to regulatory approval, of which certain early tests involve non-human animal species. In performing such tests, it is generally desirable to use as a non-human species a species bearing a high degree of genetic similarity to humans (e.g., non-human primates such as cynomolgus monkey), since the results so obtained will generally be highly predictive of corresponding results which may be expected when administering the same molecule to humans. However, such predictive power based on animal tests depends at least partially on the comparability of the molecule, and is very high if, due to a cross-species reactivity, the same therapeutic molecule may be administered to humans and non-human animals. Accordingly, if an antibody molecule is cross-reactive for the same antigen in humans and in another species, tests may be performed using the same antibody molecule in humans and in the other species, for example in one of the monkey species mentioned above. This increases both the efficiency of the tests themselves as well as the predictive power of such tests regarding the behavior of such antibodies in humans, the ultimate species of interest from a therapeutic standpoint.

The term "antibody binding to GM-CSF or to GM-CSF receptor", as used herein throughout the present text, also includes monoclonal antibodies to GM-CSF or GM-CSF receptor, or a functional fragment thereof having such binding capacity.

A first aspect of the present invention relates to a method for the treatment of an inflammatory disease in a subject suffering from the inflammatory disease, the method comprising administration of a compound neutralizing GM-CSF (briefly: GM-CSF-inhibiting compound) and a compound neutralizing IL-17 (briefly: IL-17-inhibiting compound). The compounds may be part of one composition, or they may be separate pharmaceuticals, depending on parameters well-known to the skilled artisan.

Preferred embodiments of the method are the following:

(a) A method, wherein the GM-CSF-neutralizing compound is administered to the subject prior or subsequent to the IL-17-neutralizing compound or a method wherein both compounds are administered simultaneously;

(b) A method according to the first aspect of the invention or according to (a), wherein the treated subject is an animal as defined above;

(c) A method according to the first aspect of the invention or according to (a) or (b), wherein the GM-CSF-neutralizing compound is a polypeptide, a peptidomimetic, a nucleic acid, or a small molecule;

(d) A method according to (c), wherein the polypeptide is an antibody or a functional fragment thereof binding to GM-CSF or to GM-CSF receptor; preferably, the antibody is a monoclonal antibody or a functional fragment thereof.

(e) A method according to (d), wherein the antibody is a human monoclonal antibody or a functional fragment thereof;

(f) A method according to (d) or (e), wherein the antibody or the functional fragment thereof binds to an epitope of human and non-human primate GM-CSF. The epitope is preferably a discontinuous epitope of human and non-human primate GM-CSF, the epitope preferably comprising amino acids 23-27 (RRLLN) and/or amino acids 65-77 (GLR/QGSLTKLKGPL). The variability at position 67 within the amino acid sequence stretch 65-77 reflects the heterogeneity in this position of GM-CSF between, on the one hand, human and gibbon GM-CSF (in which position 67 is R) and, on the other hand, monkeys of the macaca family, for example cynomolgous and rhesus monkeys (in which position 67 is Q);

(g) A method according to (f), wherein said discontinuous epitope further comprises amino acids 28-31 (LSRD), amino acids 32-33 (TA), and/or amino acids 21-22 (EA);

(h) A method according to any of (e), (f), and (g), wherein the human monoclonal antibody or the functional fragment thereof comprises in its heavy chain variable region a CDR3 comprising any of the amino acid sequences set out in SEQ ID NOs: 1-13 or 56;

(i) A method according to (h), wherein any of said heavy chain variable region CDR3 sequences exists together in a heavy chain variable region with the heavy chain variable region CDR1 sequence set out in SEQ ID NO: 14 and heavy chain variable region CDR2 sequence set out in SEQ ID NO: 15;

(j) A method according to (h) or (i), wherein the human monoclonal antibody or the functional fragment thereof comprises in its light chain variable region a CDR1 comprising the amino acid sequence set out in SEQ ID NO: 16, a CDR2 comprising the amino acid sequence set out in SEQ ID NO: 17, and a CDR3 comprising the amino acid sequence set out in SEQ ID NO: 18;

(k) A method according to (j), wherein the human monoclonal antibody or the functional fragment thereof further comprises in its light chain variable region an amino acid sequence as set out in any of SEQ ID NOs. 19, 54, and 55;

(l) A method according to (h) or (i), wherein the human monoclonal antibody or the functional fragment thereof comprises in its heavy chain variable region an amino acid sequence as set out in any of SEQ ID NOs: 20-33, 52 or 53;

(m) A method according to any of (h) to (l), wherein the human monoclonal antibody or the functional fragment thereof comprises in its light chain variable region a CDR1 comprising an amino acid sequence as set out in SEQ ID NO. 16, a CDR2 having an amino acid sequence as set out in SEQ ID NO. 17 and a CDR3 having an amino acid sequence as set out in SEQ ID NO. 18, and in its heavy chain variable region a CDR1 region comprising an amino acid sequence as set out in SEQ ID NO. 14, a CDR2 region having an amino acid sequence as set out in SEQ ID NO. 15 and a CDR3 having an amino acid sequence as set out in any of SEQ ID NOs. 1-13 or 56;

(n) A method according to any of (h) to (m), wherein the human monoclonal antibody or the functional fragment thereof comprises a light chain amino acid sequence as set out in SEQ ID NOs: 34 and a heavy chain amino acid sequence as set out in any of SEQ ID NOs: 35-48;

(o) A method according to any of (h) to (n), wherein the human monoclonal antibody or the functional fragment thereof comprises an amino acid sequence bearing at least 70% homology to the respective amino acid sequence as set out in any of SEQ ID NOs: 1-48 and/or 52-56. Homology is determined by standard sequence alignment programs such as Vector NTI (InforMax™, Maryland, USA). Such programs compare aligned sequences on an amino acid-by-amino acid basis, and can be set to various levels of stringency for the comparison (e.g. identical amino acid, conservative amino acid substitution, etc.). As the term is used herein, two amino acids in question are considered as being "conservative substitutions" of one another if they each belong to the same chemical class, i.e. acidic, nonpolar, uncharged polar and basic. By way of non-limiting example, two different amino acids belonging to the class of nonpolar amino acids would be considered "conservative substitutions" of one another, even if these two amino acids were not identical, whereas a nonpolar amino acid on the one hand and a basic amino acid on the other hand would not be considered "conservative substitutions" of one another. Panel 3.1 of "Molecular Biology of the Cell", 4$^{th}$ Edition (2002), by Alberts, Johnson, Lewis, Raff, Roberts and Walter groups amino acids into four main groups: acidic, nonpolar, uncharged polar and basic. Such a grouping may be used for the purposes of determining, for the purposes of the present invention, whether or not a particular amino acid is a conservative substitution of another amino acid in question;

(p) A method according to the first aspect of the invention or according to any of (a) to (o), wherein the IL-17-neutralizing compound is a polypeptide, a peptidomimetic, a nucleic acid, or a small molecule;

(q) A method according to (p), wherein the polypeptide is an antibody or a functional fragment thereof binding to IL-17 or the IL-17 receptor; preferably, the antibody is a monoclonal antibody or a functional fragment thereof.

(r) A method according to (q), wherein the antibody is a human monoclonal antibody or a functional fragment thereof; and (s) A method according to the first aspect of the invention or according to any of (a) to (r), wherein the inflammatory disease is rheumatoid arthritis (RA) (including RA which is resistant to treatment with TNF-alpha neutralizers), asthma, multiple sclerosis (MS), chronic obstructive pulmonary disease (COPD), Acute Respiratory Distress Syndrome (ARDS), Idiopathic Pulmonary Fibrosis (IPF), Inflammatory Bowel Disease (IBD), Crohn's disease, uveitis, macular degeneration, colitis, psoriasis, Wallerian Degeneration, antiphospholipid syndrome (APS), acute coronary syndrome, restinosis, atherosclerosis, relapsing polychondritis (RP), acute or chronic hepatitis, failed orthopedic implants, glomerulonephritis, lupus, or another autoimmune disorder.

A second aspect of the present invention relates to a method for the treatment of a tumorous disease in a subject suffering from the tumorous disease, the method comprising administration of a GM-CSF-neutralizing compound and an IL-17-neutralizing compound. The compounds may be part of one composition, or they may be separate pharmaceuticals, depending on parameters well-known to the skilled artisan.

Preferred embodiments of the method according to the second aspect are the following:

(a) A method, wherein the GM-CSF-neutralizing compound is administered to the subject prior or subsequent to the IL-17-neutralizing compound or a method wherein both compounds are administered simultaneously;

(b) A method according to the second aspect of the invention or according to (a), wherein the treated subject is an animal as defined above. Preferably, the subject is a human or a non-human primate;

(c) A method according to the second aspect of the invention or according to (a) or (b), wherein the GM-CSF-neutralizing compound is a polypeptide, a peptidomimetic, a nucleic acid, or a small molecule;

(d) A method according to (c), wherein the polypeptide is an antibody or a functional fragment thereof binding to GM-CSF or to GM-CSF receptor; preferably, the antibody is a monoclonal antibody or a functional fragment thereof.

(e) A method according to (d), wherein the antibody is a human monoclonal antibody or a functional fragment thereof;

(f) A method according to (d) or (e), wherein the antibody or the functional fragment thereof binds to an epitope of human and non-human primate GM-CSF. The epitope is preferably a discontinuous epitope of human and non-human primate GM-CSF, the epitope preferably comprising amino acids 23-27 (RRLLN) and/or amino acids 65-77 (GLR/QGSLTKLKGPL);

(g) A method according to (f), wherein said discontinuous epitope further comprises amino acids 28-31 (LSRD), amino acids 32-33 (TA), and/or amino acids 21-22 (EA);

(h) A method according to any of (e), (f), and (g), wherein the human monoclonal antibody or the functional fragment thereof comprises in its heavy chain variable region a CDR3 comprising any of the amino acid sequences set out in SEQ ID NOs: 1-13 or 56;

(i) A method according to (h), wherein any of said heavy chain variable region CDR3 sequences exists together in a heavy chain variable region with the heavy chain variable region CDR1 sequence set out in SEQ ID NO: 14 and heavy chain variable region CDR2 sequence set out in SEQ ID NO: 15;

(j) A method according to (h) or (i), wherein the human monoclonal antibody or the functional fragment thereof comprises in its light chain variable region a CDR1 comprising the amino acid sequence set out in SEQ ID NO: 16, a CDR2 comprising the amino acid sequence set out in SEQ ID NO: 17, and a CDR3 comprising the amino acid sequence set out in SEQ ID NO: 18;

(k) A method according to (j), wherein the human monoclonal antibody or the functional fragment thereof further comprises in its light chain variable region an amino acid sequence as set out in any of SEQ ID NOs. 19, 54, and 55;

(l) A method according to (h) or (i), wherein the human monoclonal antibody or the functional fragment thereof comprises in its heavy chain variable region an amino acid sequence as set out in any of SEQ ID NOs: 20-33, 52 or 53;

(m) A method according to any of (h) to (l), wherein the human monoclonal antibody or the functional fragment thereof comprises in its light chain variable region a CDR1 comprising an amino acid sequence as set out in SEQ ID NO. 16, a CDR2 having an amino acid sequence as set out in SEQ ID NO. 17 and a CDR3 having an amino acid sequence as set out in SEQ ID NO. 18, and in its heavy chain variable region a CDR1 region comprising an amino acid sequence as set out in SEQ ID NO. 14, a CDR2 region having an amino acid sequence as set out in SEQ ID NO. 15 and a CDR3 having an amino acid sequence as set out in any of SEQ ID NOs. 1-13 or 56;

(n) A method according to any of (h) to (m), wherein the human monoclonal antibody or the functional fragment thereof comprises a light chain amino acid sequence as set out in SEQ ID NOs: 34 and a heavy chain amino acid sequence as set out in any of SEQ ID NOs: 35-48;

(o) A method according to any of (h) to (n), wherein the human monoclonal antibody or the functional fragment thereof comprises an amino acid sequence bearing at least 70% homology to the respective amino acid sequence as set out in any of SEQ ID NOs: 1-48 and/or 52-56. Homology is defined here as in the preceding paragraph relating to the first aspect of the present invention, embodiment (o);

(p) A method according to the second aspect of the invention or according to any of (a) to (o), wherein the IL-17-neutralizing compound is a polypeptide, a peptidomimetic, a nucleic acid, or a small molecule;

(q) A method according to (p), wherein the polypeptide is an antibody or a functional fragment thereof binding to IL-17 or the IL-17 receptor; preferably the antibody is a monoclonal antibody or a functional fragment thereof;

(r) A method according to (q), wherein the antibody is a human monoclonal antibody or a functional fragment thereof;

(s) A method according to the second aspect of the invention or according to any of (a) to (r), wherein said tumorous disease is a cancer; and (t) A method according to (s), wherein said cancer is leukemia, multiple myeloma, gastric carcinoma or skin carcinoma.

A third aspect of the invention is a pharmaceutical composition for use in human and/or veterinary medicine, in particular for the treatment of an inflammatory disease or a tumorous disease in a human and/or in an animal as defined above. The composition comprises a GM-CSF-neutralizing compound (briefly: GM-CSF-inhibiting compound) and an IL-17-neutralizing compound (briefly: IL-17-inhibiting compound). Preferred embodiments of the composition according to the third aspect of the invention are as follows.

(a) A composition, wherein the GM-CSF-inhibiting compound is a polypeptide, a peptidomimetic, a nucleic acid, or a small molecule;

(b) A composition according to (a), wherein the polypeptide is an antibody or a functional fragment thereof binding to GM-CSF or to GM-CSF receptor; preferably, the antibody is a monoclonal antibody or a functional fragment thereof.

(c) A composition according to (b), wherein the antibody or the functional fragment thereof is a human monoclonal antibody or a functional fragment thereof;

(d) A composition according to (b) or (c), wherein the antibody or the functional fragment thereof binds to an epitope of human and non-human primate GM-CSF. The epitope is preferably a discontinuous epitope of human and non-human primate GM-CSF, the epitope preferably comprising amino acids 23-27 (RRLLN) and/or amino acids 65-77 (GLR/QGSLTKLKGPL);

(e) A composition according to (d), wherein said discontinuous epitope further comprises amino acids 28-31 (LSRD), amino acids 32-33 (TA), and/or amino acids 21-22 (EA);

(f) A composition according to any of (c), (d), and (e), wherein the human monoclonal antibody or the functional fragment thereof comprises in its heavy chain variable region a CDR3 comprising any of the amino acid sequences set out in SEQ ID NOs: 1-13 or 56;

(g) A composition according to (f), wherein any of said heavy chain variable region CDR3 sequences exists together in a heavy chain variable region with the heavy chain variable region CDR1 sequence set out in SEQ ID NO: 14 and heavy chain variable region CDR2 sequence set out in SEQ ID NO: 15;

(h) A composition according to (f) or (g), wherein the human monoclonal antibody or the functional fragment thereof comprises in its light chain variable region a CDR1 comprising the amino acid sequence set out in SEQ ID NO: 16, a CDR2 comprising the amino acid sequence set out in SEQ ID NO: 17, and a CDR3 comprising the amino acid sequence set out in SEQ ID NO: 18;

(i) A composition according to (h), wherein the human monoclonal antibody or the functional fragment thereof further comprises in its light chain variable region an amino acid sequence as set out in any of SEQ ID NOs. 19, 54, and 55;

(j) A composition according to (f) or (g), wherein the human monoclonal antibody or the functional fragment thereof comprises in its heavy chain variable region an amino acid sequence as set out in any of SEQ ID NOs: 20-33, 52 or 53;

(k) A composition according to any of (f) to (j), wherein the human monoclonal antibody or the functional fragment thereof comprises in its light chain variable region a CDR1 comprising an amino acid sequence as set out in SEQ ID NO. 16, a CDR2 having an amino acid sequence as set out in SEQ ID NO. 17 and a CDR3 having an amino acid sequence as set out in SEQ ID NO. 18, and in its heavy chain variable region a CDR1 region comprising an amino acid sequence as set out in SEQ ID NO. 14, a CDR2 region having an amino acid sequence as set out in SEQ ID NO. 15 and a CDR3 having an amino acid sequence as set out in any of SEQ ID NOs. 1-13 or 56;

(l) A composition according to any of (f) to (k), wherein the human monoclonal antibody or the functional fragment thereof comprises a light chain amino acid sequence as set out in SEQ ID NOs: 34 and a heavy chain amino acid sequence as set out in any of SEQ ID NOs: 35-48;

(m) A composition according to any of (f) to (l), wherein the human monoclonal antibody or the functional fragment thereof comprises an amino acid sequence bearing at least 70% homology to the respective amino acid sequence as set out in any of SEQ ID NOs: 1-48 and/or 52-56. Homology is defined here as in the preceding paragraph relating to the first aspect of the present invention, embodiment (o);

(n) A composition according to any of (a) to (m), wherein the IL-17-inhibiting compound is a polypeptide, a peptidomimetic, a nucleic acid, or a small molecule;

(o) A composition according to (n), wherein the polypeptide is an antibody or a functional fragment thereof binding to IL-17 or the IL-17 receptor; preferably, the antibody is a monoclonal antibody or a functional fragment thereof;

(p) A composition according to (o), wherein the antibody or the functional fragment thereof is a human monoclonal antibody or a functional fragment thereof, respectively;

(q) A composition according to any of (a) to (p), wherein said composition is for the treatment of an inflammatory disease and/or a tumorous disease, in particular wherein the inflammatory disease is rheumatoid arthritis (RA) (including RA which is resistant to treatment with TNF-alpha neutralizers), asthma, multiple sclerosis (MS), chronic obstructive pulmonary disease (COPD), Acute Respiratory Distress Syndrome (ARDS), Idiopathic Pulmonary Fibrosis (IPF), Inflammatory Bowel Disease (IBD), Crohn's disease, uveitis, macular degeneration, colitis, psoriasis, Wallerian Degeneration, antiphospholipid syndrome (APS), acute coronary syndrome, restinosis, atherosclerosis, relapsing polychondritis (RP), acute or chronic hepatitis, failed orthopedic implants, glomerulonephritis, lupus, or an autoimmune disorder, and/or the tumorous disease is a cancer such as leukemia, multiple myeloma, gastric carcinoma or skin carcinoma, and/or wherein said tumorous disease is cancer such as leukemia, multiple myeloma, gastric carcinoma or skin carcinoma.

Depending on the jurisprudence where this application is to be filed, a fourth aspect of the invention may be the combined use of a GM-CSF-inhibiting compound and an IL-17-inhibiting compound in the manufacture of a pharmaceutical for the treatment of inflammatory diseases and tumorous diseases, as further specified above. Accordingly, in a preferred embodiment of the fourth aspect of the present invention the pharmaceutical comprising the GM-CSF- and IL-17-inhibiting compound may be formulated for administration of (i) first the GM-CSF-inhibiting compound and second the IL-17-inhibiting compound, (ii) first the IL-17-inhibiting compound and second the GM-CSF-inhibiting compound, and (iii) the GM-CSF-inhibiting compound and the IL-17-inhibiting compound simultaneously. Accordingly, the two compounds may be part of one composition, or they may be separate pharmaceuticals, depending on parameters well-known to the skilled artisan.

In the alternative, a fifth aspect may be the GM-CSF- and the IL-17-inhibiting compound for use in treating any of the diseases as detailed above. Again, administration of the compounds may be one after the other in any order or may be simultaneously. Likewise, the compounds may be part of one composition, or they may be separate pharmaceuticals, depending on parameters well-known to the skilled artisan.

The preferred embodiments in case of using the GM-CSF- and IL-17-inhibiting compound in the manufacture of a pharmaceutical and in case of the GM-CSF- and the IL-17-inhibiting compound for use in treating any of the diseases are the following:

(a) The subject to be treated has been defined above;
(b) The GM-CSF-inhibiting compound is a polypeptide, a peptidomimetic, a nucleic acid, or a small molecule;
(c) The polypeptide according to (b) is an antibody or a functional fragment thereof binding to GM-CSF or to GM-CSF receptor; preferably, the antibody is a monoclonal antibody or a functional fragment thereof.

(d) The antibody or the functional fragment thereof, as defined in (c), is a human monoclonal antibody or a functional fragment thereof;

(e) The antibody or the functional fragment thereof binds to an epitope of human and non-human primate GM-CSF. The epitope is preferably a discontinuous epitope of human and non-human primate GM-CSF, the epitope preferably comprising amino acids 23-27 (RRLLN) and/or amino acids 65-77 (GLR/QGSLTKLKGPL).

(f) The discontinuous epitope further comprises amino acids 28-31 (LSRD), amino acids 32-33 (TA), and/or amino acids 21-22 (EA);

(g) The human monoclonal antibody or the functional fragment thereof according to any of (d), (e), and (f) comprises in its heavy chain variable region a CDR3 comprising any of the amino acid sequences set out in SEQ ID NOs: 1-13 or 56;

(h) Embodiment (g), wherein any of said heavy chain variable region CDR3 sequences exists together in a heavy chain variable region with the heavy chain variable region CDR1 sequence set out in SEQ ID NO: 14 and heavy chain variable region CDR2 sequence set out in SEQ ID NO: 15;

(i) Embodiment (h) or (g), wherein the human monoclonal antibody or the functional fragment thereof comprises in its light chain variable region a CDR1 comprising the amino acid sequence set out in SEQ ID NO: 16, a CDR2 comprising the amino acid sequence set out in SEQ ID NO: 17, and a CDR3 comprising the amino acid sequence set out in SEQ ID NO: 18;

(j) The human monoclonal antibody or the functional fragment thereof according to (i) further comprises in its light chain variable region an amino acid sequence as set out in any of SEQ ID NOs. 19, 54, and 55;

(k) The human monoclonal antibody or the functional fragment thereof according to embodiment (h) or (g) comprises in its heavy chain variable region an amino acid sequence as set out in any of SEQ ID NOs: 20-33, 52 or 53;

(l) Any of embodiments (g) to (k), wherein the human monoclonal antibody or the functional fragment thereof comprises in its light chain variable region a CDR1 comprising an amino acid sequence as set out in SEQ ID NO. 16, a CDR2 having an amino acid sequence as set out in SEQ ID NO. 17 and a CDR3 having an amino acid sequence as set out in SEQ ID NO. 18, and in its heavy chain variable region a CDR1 region comprising an amino acid sequence as set out in SEQ ID NO. 14, a CDR2 region having an amino acid sequence as set out in SEQ ID NO. 15 and a CDR3 having an amino acid sequence as set out in any of SEQ ID NOs. 1-13 or 56;

(m) Any of embodiments (g) to (l), wherein the human monoclonal antibody or the functional fragment thereof comprises a light chain amino acid sequence as set out in SEQ ID NOs: 34 and a heavy chain amino acid sequence as set out in any of SEQ ID NOs: 35-48;

(n) Any of embodiments (g) to (m), wherein the human monoclonal antibody or the functional fragment thereof comprises an amino acid sequence bearing at least 70% homology to the respective amino acid sequence as set out in any of SEQ ID NOs: 1-48 and/or 52-56. Homology is determined by standard sequence alignment programs such as Vector NTI (InforMax™, Maryland, USA). Such programs compare aligned sequences on an amino acid-by-amino acid basis, and can be set to various levels of stringency for the comparison (e.g. identical amino acid, conservative amino acid substitution, etc.). As the term is used herein, two amino acids in question are considered as being "conservative substitutions" of one another if they each belong to the same chemical class, i.e. acidic, nonpolar, uncharged polar and basic. By way of non-limiting example, two different amino acids belonging to the class of nonpolar amino acids would be considered "conservative substitutions" of one another, even if these two amino acids were not identical, whereas a nonpolar amino acid on the one hand and a basic amino acid on the other hand would not be considered "conservative substitutions" of one another. Panel 3.1 of "Molecular Biology of the Cell", 4$^{th}$ Edition (2002), by Alberts, Johnson, Lewis, Raff, Roberts and Walter groups amino acids into four main groups: acidic, nonpolar, uncharged polar and basic. Such a grouping may be used for the purposes of determining, for the purposes of the present invention, whether or not a particular amino acid is a conservative substitution of another amino acid in question;

(o) Any of embodiments (a) to (n), wherein the IL-17-inhibiting compound is a polypeptide, a peptidomimetic, a nucleic acid, or a small molecule;

(p) The polypeptide of (o) is an antibody or a functional fragment thereof binding to IL-17 or the IL-17 receptor; preferably, the antibody is a monoclonal antibody or a functional fragment thereof;

(q) The antibody or the functional fragment thereof of (p) is a human monoclonal antibody or a functional fragment thereof; and (r) The inflammatory disease is rheumatoid arthritis (RA) (including RA which is resistant to treatment with TNF-alpha neutralizers), asthma, multiple sclerosis (MS), chronic obstructive pulmonary disease (COPD), Acute Respiratory Distress Syndrome (ARDS), Idiopathic Pulmonary Fibrosis (IPF), Inflammatory Bowel Disease (IBD), Crohn's disease, uveitis, macular degeneration, colitis, psoriasis, Wallerian Degeneration, antiphospholipid syndrome (APS), acute coronary syndrome, restinosis, atherosclerosis, relapsing polychondritis (RP), acute or chronic hepatitis, failed orthopedic implants, glomerulonephritis, lupus, or an autoimmune disorder; and/or the tumurous disease is cancer such as leukemia, multiple myeloma, gastric carcinoma or skin carcinoma.

As mentioned before, the term "IL-17", as used in the present application refers to a family of cytokines of the acquired immune system, consisting of six members, IL-17A to IL-17F. The definition of the term also comprises heterodimers such as IL-17A/IL-17F, which have been reported as being physiologically expressed e.g. by CD4$^+$ T cells. A particularly preferred group of the IL-17 family members to be neutralized in accordance with the invention comprises IL-17A, IL-17F and IL-17D. More preferably, the effects of IL-17A and IL-17F are neutralized accordance with the invention. Since the group consisting of the IL-17A, IL-17F and IL-17D is preferred, it is also preferred to neutralize/inhibit the signaling of a subgroup of IL-17 receptors (IL-17Rs), i.e. the signaling of IL-17RA, IL-17RB and IL-17RC, more preferably of IL-17RA and IL-17RC.

The term "specifically binds" or related expressions such as "specific binding", "binding specifically", "specific binder" etc. as used herein refer to the ability of the GM-CSF-/IL-17-inhibiting compound and preferably the human monoclonal antibody or functional fragment thereof (as defined previously) to discriminate between GM-CSF/IL-17 and any number of other potential antigens different from GM-CSF/IL-17 to such an extent that, from a pool of a plurality of different antigens as potential binding partners, only GM-CSF/IL-17 is bound, or is significantly bound. Within the meaning of the invention, GM-CSF/IL-17 is "significantly" bound when, from among a pool of a plurality of equally accessible different antigens as potential binding partners, GM-CSF/IL-17 is bound at least 10-fold, preferably 50-fold, most preferably 100-fold or greater more frequently (in a kinetic sense) than any other antigen different than GM-CSF/IL-17. Such kinetic measurements can be performed on a Biacore apparatus.

As used herein, "neutralization", "neutralizer", "neutralizing" and grammatically related variants thereof refer to partial or complete attenuation of the biological effect(s) of GM-CSF/IL-17. Such partial or complete attenuation of the biological effect(s) of GM-CSF/IL-17 results from modification, interruption and/or abrogation of GM-CSF/IL-17-mediated processes such as signal transduction, as manifested, for example, in intracellular signaling, cellular proliferation or release of soluble substances, up- or down-regulation of intracellular gene activation, for example that resulting in expression of surface receptors for ligands other than GM-CSF. As one of skill in the art understands, there exist multiple modes of determining whether an agent, for example an antibody in question or functional fragment thereof is to be classified as a neutralizer. As an example, this may be accomplished by a standard in vitro test performed generally as follows: In a first proliferation experiment, a cell line, the degree of proliferation of which is known to depend on the activity of GM-CSF, is incubated in a series of samples with varying concentrations of GM-CSF, following which incubation the degree of proliferation of the cell line is measured. From this measurement, the concentration of GM-CSF allowing half-maximal proliferation of the cells is determined. A second proliferation experiment is then performed employing in each of a series of samples the same number of cells as used in the first proliferation experiment, the above-determined concentration of GM-CSF and, this time, varying concentrations of an antibody or functional fragment thereof suspected of being a neutralizer of GM-CSF. Cell proliferation is again measured to determine the concentration of antibody or functional fragment thereof sufficient to effect half-maximal growth inhibition. If the resulting graph of growth inhibition vs. concentration of antibody (or functional fragment thereof) is sigmoidal in shape, resulting in decreased cell proliferation with increasing concentration of antibody (or functional fragment thereof), then some degree of antibody-dependent growth inhibition has been effected, i.e. the activity of GM-CSF has been neutralized to some extent. In such a case, the antibody or functional fragment thereof may be considered a "neutralizer" in the sense of the present invention. One example of a cell line, the degree of proliferation of which is known to depend on the activity of GM-CSF, is the TF-1 cell line, as described in Kitamura, T. et al. (1989). J Cell Physiol 140, 323-34.

As one of ordinary skill in the art understands, the degree of cellular proliferation is not the only parameter by which the GM-CSF neutralizing capacity may be established. For example, measurement of the level of signaling molecules (e.g. cytokines), the level of secretion of which depends on GM-CSF, may be used to identify a suspected GM-CSF neutralizer (GM-CSF inhibiting compound). Corresponding cellular experimental settings are known by the person skilled in the art for the verification of the neutralizing effects of an IL-17 inhibiting compound.

Other examples of cell lines which can be used to determine whether an antibody in question or functional fragment thereof, which is a neutralizer of GM-CSF activity, include AML-193 (Lange, B. et al. (1987). Blood 70, 192-9); GF-D8 (Rambaldi, A. et al. (1993). Blood 81, 1376-83); GM/SO (Oez, S. et al. (1990). Experimental Hematology 18, 1108-11); MOTE (Avanzi, G. C. et al. (1990). Journal of Cellular Physiology 145, 458-64); TALL-103 (Valtieri, M. et al. (1987). Journal of Immunology 138, 4042-50); UT-7 (Komatsu, N. et al. (1991). Cancer Research 51, 341-8). Examples for cell lines/cell based assays which can be used to determine whether compound in question, e.g. an antibody or functional fragment thereof, is a neutralizer of IL-17 activity include a BEAS-2B in Vitro Assay of IL-17 Proteins (BEAS-2B, human bronchial epithelial cells (ATCC, CRL-9609) or a standard IL-6 release assay from fibroblasts (Yao et al., 1995, Journal of Immunology, 155, 5483-5486).

It is understood that an inhibition/neutralization of GM-CSF and IL-17, respectively, in line with the present invention can be effected either outside the cells bearing the receptors for these cytokines or in said cells. Thus, the inhibition/neutralization of GM-CSF and IL-17 by a compound can either be an inhibition or prevention of the binding of GM-CSF or IL-17 to its specific receptor or an inhibition of the intracellular signal induced by a binding of the cytokines to its receptors. Example for intracellular acting inhibitors/neutralizers of the IL-17 signal comprise compounds which block the intracellular signal pathways, include inhibitors of JAK/STAT, MAPK p38, NF-kappaB or JNK.

As defined herein above, inhibitors of GM-CSF or IL-17 can be selected from the group consisting of a polypeptide, a peptidomimetic, a nucleic acid molecule, and a small molecule. The term "polypeptide" as used herein describes a group of molecules, which consist of more than 30 amino acids. In accordance with the invention, the group of polypeptides comprises "proteins" consisting of a single polypeptide or more than one polypeptide. The term "polypeptide" also describes fragments of proteins as long as these fragments consist of more than 30 amino acids. It is well known in the art that polypeptides may form multimers such as dimers, trimers and higher oligomers, i.e. consisting of more than one polypeptide molecule. Such multimers are also included in the definition of the term "polypeptide". Polypeptide molecules forming such dimers, trimers etc. may be identical or non-identical. The corresponding higher order structures of such multimers are, consequently, termed homo- or heterodimers, homo- or heterotrimers etc. An example for a hereteromultimer is an antibody molecule, which, in its naturally occurring form, consists of two identical light polypeptide chains and two identical heavy polypeptide chains. The terms "polypeptide" and "protein" also refer to naturally or non-naturally modified polypeptides/proteins wherein the modification is effected e.g. by post-translational modifications like glycosylation, acetylation, phosphorylation and the like. Such modifications are well known in the art.

The term "small molecule" defines a group of drug compounds having a molecular weight of less than 1000 Daltons, and preferably of 300 to 700 Daltons. Corresponding small molecules can be derived from an at least partially randomized peptide library. Libraries of small molecules suitable according to the present invention are well known in the art and/or can be purchased form commercial distributors.

The term "nucleic acid" defines in the context of the invention macromolecules consisting of multiply repeat units of phosphoric acid, sugar and purine and pyrimidine bases. Embodiments of these molecules include DNA, RNA and PNA. A particularly preferred embodiment of a nucleic acid in the context of the invention is an aptamer. Aptamers are DNA or RNA molecules that have been selected from random pools based on their ability to bind other molecules. Aptamers have been selected which bind nucleic acid, proteins, small organic compounds, and even entire organisms.

The term "peptidomimetic" describes a small protein-like chain designed to mimic a peptide. This type of molecule is artificially derived by modifying an existing peptide in order to alter the molecule's properties. For example, the parent existing peptide is modified to change the molecule's stability or biological activity. These modifications comprise the alteration of the backbone and the incorporation of nonnatural amino acids.

The term "GM-CSF receptor" refers to the physiological cell surface receptor of GM-CSF, which is described in the art as a heteromer of CD116 and a common beta (βc) subunit. The term "IL-17 receptor" refers to the family of physiological cell surface receptors of the different isoforms of IL-17. This family presently comprises inter alia the isoforms IL-17RA, IL-17RB, IL-17RC, IL-17RD and IL-17RE.

A preferred embodiment of a neutralizing peptide is an antibody (or functional fragments thereof), more preferably a human antibody (or functional fragments thereof). Techniques for the production of antibodies are well known in the art and described, e.g. in Harlow and Lane "Antibodies, A Laboratory Manual", Cold Spring Harbor Laboratory Press, 1988 and Harlow and Lane "Using Antibodies: A Laboratory Manual" Cold Spring Harbor Laboratory Press, 1999. The term "antibody" comprises immunoglobulins (Ig's) of different classes (i.e. IgA, IgG, IgM, IgD and IgE) and subclasses (such as IgG1, IgG2 etc.). Derivatives of antibodies, which also fall under the definition of the term antibody in the meaning of the invention, include modifications of such molecules as for example glycosylation, acetylation, phosphorylation, farnesylation, hydroxylation, methylation or esterification.

The non-human and human antibodies or functional fragments thereof (with specificity for both GM-CSF and IL-17) are preferably monoclonal. It is particularly difficult to prepare human antibodies which are monoclonal. In contrast to fusions of murine B cells with immortalized cell lines, fusions of human B cells with immortalized cell lines are not viable. Thus, the human monoclonal antibodies are the result of overcoming significant technical hurdles generally acknowledged to exist in the field of antibody technology. The monoclonal nature of the antibodies makes them particularly well suited for use as therapeutic agents, since such antibodies will exist as a single, homogeneous molecular species which can be well-characterized and reproducibly made and purified. These factors result in products whose biological activities can be predicted with a high level of precision, very important if such molecules are going to gain regulatory approval for therapeutic administration in humans.

It is especially preferred that the monoclonal antibodies (or corresponding functional fragments) be human antibodies (or corresponding functional fragments). In contemplating antibody agents intended for therapeutic administration to humans, it is highly advantageous that the antibodies are of human origin. Following administration to a human patient, a human antibody or functional fragment thereof will most probably not elicit a strong immunogenic response by the patient's immune system, i.e. will not be recognized as being a foreign that is non-human protein. This means that no host, i.e. patient, antibodies will be generated against the therapeutic antibody which would otherwise block the therapeutic antibody's activity and/or accelerate the therapeutic antibody's elimination from the body of the patient, thus preventing it from exerting its desired therapeutic effect.

The term "human" antibody as used herein is to be understood as meaning that the antibody with either specificity, or its functional fragment, comprises (an) amino acid sequence(s) contained in the human germline antibody repertoire. For the purposes of definition herein, an antibody, or its fragment, may therefore be considered human if it consists of such (a) human germline amino acid sequence(s), i.e. if the amino acid sequence(s) of the antibody in question or functional fragment thereof is (are) identical to (an) expressed human germline amino acid sequence(s). An antibody or functional fragment thereof may also be regarded as human if it consists of (a) sequence(s) that deviate(s) from its (their) closest human germline sequence(s) by no more than would be expected due to the imprint of somatic hypermutation. Additionally, the antibodies of many non-human mammals, for example rodents such as mice and rats, comprise VH CDR3 amino acid sequences which one may expect to exist in the expressed human antibody repertoire as well. Any such sequence(s) of human or non-human origin which may be expected to exist in the expressed human repertoire would also be considered "human" for the purposes of the present invention.

According to a preferred embodiment of the invention, the human monoclonal antibody or functional fragment thereof to be utilized for pharmaceutical purposes exhibits cross-reactivity between both human and at least one monkey species. The same cross-species reactivity is also preferred for all other (non-antibody or non-antibody derived) neutralizing/inhibiting compounds of GM-CSF and/or IL-17. Since pharmaceuticals will normally have to proceed through a multitude of tests prior to regulatory approval, of which certain early tests involve non-human animal species, such cross-reacting antibodies are very useful. In performing such tests, it is generally desirable to use as a non-human species a species bearing a high degree of genetic similarity to humans, since the results so obtained will generally be highly predictive of corresponding results which may be expected when administering the same molecule to humans. However, such predictive power based on animal tests depends at least partially on the comparability of the molecule, and is very high when, due to a cross-species reactivity, the same therapeutic molecule may be administered to humans and animal models. As in the embodiment, when an antibody molecule is cross-reactive for the same antigen in humans as in another closely related species, tests may be performed using the same antibody molecule in humans as in this closely related species, for example in a monkey species mentioned above. This increases both the efficiency of the tests themselves as well as predictive power allowed by such tests regarding the behavior of such antibodies in humans, the ultimate species of interest from a therapeutic standpoint. The same holds true for alternative embodiments with neutralizing/inhibiting compounds, which are not antibodies (or not antibody derived).

According to a further embodiment of the invention, the human monoclonal antibody may be an IgG antibody. An IgG comprises not only the variable antibody regions responsible for the highly discriminative antigen recognition and binding, but also the constant regions of the heavy and light antibody polypeptide chains normally present in endogenously produced antibodies and, in some cases, even decoration at one or more sites with carbohydrates. Such glycosylation is generally a hallmark of the IgG format, and portions of these constant regions make up the so called Fc region of a full antibody which is known to elicit various effector functions in vivo. In addition, the Fc region mediates binding of IgG to Fc receptor, hence prolonging half life in vivo as well as facilitating homing of the IgG to locations with increased Fc receptor presence—inflamed tissue, for example. Advantageously, the IgG antibody is an IgG1 antibody or an IgG4 antibody, formats which are preferred since their mechanism of action in vivo is particularly well understood and characterized. This is especially the case for IgG1 antibodies.

According to a further embodiment of the invention, the functional fragment of the human monoclonal antibody may be an scFv, a single domain antibody, an Fv, a VHH antibody, a diabody, a tandem diabody, a Fab, a Fab' or a F(ab)2. These formats may generally be divided into two subclasses, namely those which consist of a single polypeptide chain, and those which comprise at least two polypeptide chains. Members of the former subclass include a scFv (comprising one VH region and one VL region joined into a single polypeptide chain via a polypeptide linker); a single domain antibody (comprising a single antibody variable region) such as a VHH antibody (comprising a single VH region). Members of the latter subclass include an Fv (comprising one VH region and one VL region as separate polypeptide chains which are non-covalently associated with one another); a diabody (comprising two non-covalently associated polypeptide chains, each of which comprises two antibody variable regions—normally one VH and one VL per polypeptide chain—the two polypeptide chains being arranged in a head-to-tail conformation so that a bivalent antibody molecule results); a tandem diabody (bispecific single-chain Fv antibodies comprising four covalently linked immunoglobulin variable—VH and VL—regions of two different specificities, forming a homodimer that is twice as large as the diabody described above); a Fab (comprising as one polypeptide chain an entire antibody light chain, itself comprising a VL region and the entire light chain constant region and, as another polypeptide chain, a part of an antibody heavy chain comprising a complete VH region and part of the heavy chain constant region, said two polypeptide chains being intermolecularly connected via an interchain disulfide bond); a Fab' (as a Fab, above, except with additional reduced disulfide bonds comprised on the antibody heavy chain); and a F(ab)2 (comprising two Fab' molecules, each Fab' molecule being linked to the respective other Fab' molecule via interchain disulfide bonds). In general, functional antibody fragments of the type described hereinabove allow great flexibility in tailoring, for example, the pharmacokinetic properties of an antibody desired for therapeutic administration to the particular exigencies at hand. For example, it may be desirable to reduce the size of the antibody administered in order to increase the degree of tissue penetration when treating tissues known to be poorly vascularized (for example, joints). Under some circumstances, it may also be desirable to increase the rate at which the therapeutic antibody is eliminated from the body, said rate generally being acceleratable by decreasing the size of the antibody administered. An antibody fragment is defined as a functional antibody fragment in the context of the invention as long as the fragment maintains the specific binding characteristics for the epitope/target of the parent antibody, i.e. as long as it specifically binds to GM-CSF or IL-17, respectively.

According to a further embodiment of the invention, said human monoclonal antibody or functional fragment thereof may be present in monovalent monospecific; multivalent monospecific, in particular bivalent monospecific; or multivalent multispecific, in particular bivalent bispecific forms. In general, a multivalent monospecific, in particular bivalent monospecific antibody such as a full human IgG as described hereinabove may bring with it the therapeutic advantage that the neutralization effected by such an antibody is potentiated by avidity effects, i.e. binding by the same antibody to multiple molecules of the same antigen, here GM-CSF/IL-17. Several monovalent monospecific forms of fragments of antibodies have been described above (for example, an scFv, an Fv, a VHH or a single domain antibody). Multivalent multispecific, in particular bivalent bispecific forms of the human monoclonal anti-GM-CSF/IL-17 antibody may include a full IgG in which one binding arm binds to non-human primate GM-CSF/IL-17 while the other binding arm of which binds to another antigen different from GM-CSF/IL-17. A further multivalent multispecific, in particular bivalent bispecific form may advantageously be a human single chain bispecific antibody, i.e. a recombinant human antibody construct comprising two scFv entities as described above, connected into one contiguous polypeptide chain by a short interposed polypeptide spacer as generally known in the art (see for example WO 99/54440 for an anti-CD19× anti-CD3 bispecific single chain antibody). Here, one scFv portion of the bispecific single chain antibody comprised within the bispecific single chain antibody will specifically bind GM-CSF/IL-17 as set out above, while the respective other scFv portion of this bispecific single chain antibody will bind another antigen determined to be of therapeutic benefit. A preferred alternative is wherein the bispecific single chain antibody will specifically bind GM-CSF as set out above, while the respective other scFv portion of this bispecific single chain antibody will bind IL-17.

According to a further embodiment the inhibitory human monoclonal antibodies or functional fragments thereof may be derivatized, for example with an organic polymer, for example with one or more molecules of polyethylene glycol ("PEG") and/or polyvinyl pyrrolidone ("PVP"). As is known in the art, such derivatization can be advantageous in modulating the pharmacodynamic properties of antibodies or functional fragments thereof. Especially preferred are PEG molecules derivatized as PEG-maleimide, enabling conjugation with the antibody or functional fragment thereof in a site-specific manner via the sulfhydryl group of a cysteine amino acid. Of these, especially preferred are 20 kD and/or 40 kD PEG-maleimide, in either branched or straight-chain form. It may be especially advantageous to increase the effective molecular weight of smaller human anti-GM-CSF/IL-17 antibody fragments such as scFv fragments by coupling the latter to one or more molecules of PEG, especially PEG-maleimide.

As used herein, the numbering of human and non-human primate GM-CSF refers to that of mature GM-CSF, i.e., GM-CSF without its 17 amino acid signal sequence (the total length of mature GM-CSF in both human and non-human primate species described above is 127 amino acids). The sequence of human GM-CSF (SEQ ID NO. 57) and gibbon GM-CSF (SEQ ID NO. 58) is as follows:

```
APARSPSPST QPWEHVNAIQ EARRLLNLSR DTAAEMNETV

EVISEMFDLQ EPTCLQTRLE LYKQGLRGSL TKLKGPLTMM

ASHYKQHCPP TPETSCATQI ITFESFKENL KDFLLVIPFD

CWEPVQE
```

The sequence of GM-CSF in certain members of the macaca monkey family such as for example rhesus monkey (SEQ ID NO. 59) and cynomolgous monkey (SEQ ID NO. 60) is as follows:

```
APARSPSPGT QPWEHVNAIQ EARRLLNLSR DTAAEMNKTV

EVVSEMFDLQ EPSCLQTRLE LYKQGLQGSL TKLKGPLTMM

ASHYKQHCPP TPETSCATQI ITFQSFKENL KDFLLVIPFD

CWEPVQE
```

The minimum epitope, advantageously a discontinuous epitope, bound by the human monoclonal antibody (or functional fragment thereof) as described above is indicated in the above GM-CSF sequence in boldface. As used herein, the term "discontinuous epitope" is to be understood as at least two non-adjacent amino acid sequence stretches within a given polypeptide chain, here mature human and non-human primate GM-CSF, which are simultaneously and specifically bound by an antibody. According to this definition, such simultaneous specific binding may be of the GM-CSF polypeptide in linear form. Here, one may imagine the mature GM-CSF polypeptide forming an extended loop, in one region of which the two sequences indicated in boldface above line up, for example more or less in parallel and in proximity of one another. In this state they are specifically and simultaneously bound by the antibody fragment. According to this definition, simultaneous specific binding of the two sequence stretches of mature GM-CSF indicated above may also take the form of antibody binding to a conformational epitope. Here, mature GM-CSF has already formed its tertiary conformation as it normally exists in vivo. In this tertiary conformation, the polypeptide chain of mature GM-CSF is folded in such a manner as to bring the two sequence stretches indicated above into spatial proximity, for example on the outer surface of a particular region of mature, folded GM-CSF, where they are then recognized by virtue of their three-dimensional conformation in the context of the surrounding polypeptide sequences.

Preferred human monoclonal anti-GM-CSF antibodies or functional fragments thereof are those comprising a heavy chain variable region CDR1 sequence as set out in SEQ ID NO: 14, a heavy chain variable region CDR2 sequence as set out in SEQ ID NO: 15 and a heavy chain variable region CDR3 sequence as set out in SEQ ID NO: 1; or comprising a heavy chain variable region CDR1 sequence as set out in SEQ ID NO: 14, a heavy chain variable region CDR2 sequence as set out in SEQ ID NO: 15 and a heavy chain variable region CDR3 sequence as set out in SEQ ID NO: 2; or comprising a heavy chain variable region CDR1 sequence as set out in SEQ ID NO: 14, a heavy chain variable region CDR2 sequence as set out in SEQ ID NO: 15 and a heavy chain variable region CDR3 sequence as set out in SEQ ID NO: 3; or comprising a heavy chain variable region CDR1 sequence as set out in SEQ ID NO: 14, a heavy chain variable region CDR2 sequence as set out in SEQ ID NO: 15 and a heavy chain variable region CDR3 sequence as set out in SEQ ID NO: 4; or comprising a heavy chain variable region CDR1 sequence as set out in SEQ ID NO: 14, a heavy chain variable region CDR2 sequence as set out in SEQ ID NO: 15 and a heavy chain variable region CDR3 sequence as set out in SEQ ID NO: 5; or comprising a heavy chain variable region CDR1 sequence as set out in SEQ ID NO: 14, a heavy chain variable region CDR2 sequence as set out in SEQ ID NO: 15 and a heavy chain variable region CDR3 sequence as set out in SEQ ID NO: 6; or comprising a heavy chain variable region CDR1 sequence as set out in SEQ ID NO: 14, a heavy chain variable region CDR2 sequence as set out in SEQ ID NO: 15 and a heavy chain variable region CDR3 sequence as set out in SEQ ID NO: 7; or comprising a heavy chain variable region CDR1 sequence as set out in SEQ ID NO: 14, a heavy chain variable region CDR2 sequence as set out in SEQ ID NO: 15 and a heavy chain variable region CDR3 sequence as set out in SEQ ID NO: 8; or comprising a heavy chain variable region CDR1 sequence as set out in SEQ ID NO: 14, a heavy chain variable region CDR2 sequence as set out in SEQ ID NO: 15 and a heavy chain variable region CDR3 sequence as set out in SEQ ID NO: 9; or comprising a heavy chain variable region CDR1 sequence as set out in SEQ ID NO: 14, a heavy chain variable region CDR2 sequence as set out in SEQ ID NO: 15 and a heavy chain variable region CDR3 sequence as set out in SEQ ID NO: 10; or comprising a heavy chain variable region CDR1 sequence as set out in SEQ ID NO: 14, a heavy chain variable region CDR2 sequence as set out in SEQ ID NO: 15 and a heavy chain variable region CDR3 sequence as set out in SEQ ID NO: 11; or comprising a heavy chain variable region CDR1 sequence as set out in SEQ ID NO: 14, a heavy chain variable region CDR2 sequence as set out in SEQ ID NO: 15 and a heavy chain variable region CDR3 sequence as set out in SEQ ID NO: 12; or comprising a heavy chain variable region CDR1 sequence as set out in SEQ ID NO: 14, a heavy chain variable region CDR2 sequence as set out in SEQ ID NO: 15 and a heavy chain variable region CDR3 sequence as set out in SEQ ID NO: 13; or comprising a heavy chain variable region CDR1 sequence as set out in SEQ ID NO: 14, a heavy chain variable region CDR2 sequence as set out in SEQ ID NO: 15 and a heavy chain variable region CDR3 sequence as set out in SEQ ID NO: 56.

Still more preferred, any of the above 14 combinations of CDR1, CDR2 and CDR3 sequences exists in a human monoclonal antibody or functional fragment thereof further comprising in its light chain variable region a CDR1 comprising the amino acid sequence set out in SEQ ID NO: 16, a CDR2 comprising the amino acid sequence set out in SEQ ID NO: 17, and a CDR3 comprising the amino acid sequence set out in SEQ ID NO: 18.

According to a further embodiment, the inhibitory human monoclonal anti-GM-CSF antibody or functional fragment thereof comprises in its light chain variable region an amino acid sequence as set out in SEQ ID NO. 19. Preferred is a human monoclonal antibody or functional fragment thereof, the light chain variable region comprising an amino acid sequence as set out in SEQ ID NO. 19 and a heavy chain variable region comprising an amino acid sequence as set out in SEQ ID NO: 20; or a human monoclonal antibody or functional fragment thereof, the light chain variable region comprising an amino acid sequence as set out in SEQ ID NO. 19 and a heavy chain variable region comprising an amino acid sequence as set out in SEQ ID NO: 21; or a human monoclonal antibody or functional fragment thereof, the light chain variable region comprising an amino acid sequence as set out in SEQ ID NO. 19 and a heavy chain variable region comprising an amino acid sequence as set out in SEQ ID NO: 22; or a human monoclonal antibody or functional fragment thereof, the light chain variable region comprising an amino acid sequence as set out in SEQ ID NO. 19 and a heavy chain variable region comprising an amino acid sequence as set out in SEQ ID NO: 23; or a human monoclonal antibody or functional fragment thereof, the light chain variable region comprising an amino acid sequence as set out in SEQ ID NO. 19 and a heavy chain variable region comprising an amino acid sequence as set out in SEQ ID NO: 24; or a human monoclonal antibody or functional fragment thereof, the light chain variable region comprising an amino acid sequence as set out in SEQ ID NO. 19 and a heavy chain variable region comprising an amino acid sequence as set out in SEQ ID NO: 25; or a human monoclonal antibody or functional fragment thereof, the light chain variable region comprising an amino acid sequence as set out in SEQ ID NO. 19 and a heavy chain variable region comprising an amino acid sequence as set out in SEQ ID NO: 26; or a human monoclonal antibody or functional fragment thereof, the light chain variable region comprising an amino acid sequence as set out in SEQ ID NO. 19 and a heavy chain variable region comprising an amino acid sequence as set out in SEQ ID NO: 27; or a human monoclonal antibody or functional fragment thereof, the light chain variable region comprising an amino acid sequence as set out in SEQ ID NO. 19 and a heavy chain variable region comprising an amino acid sequence as set out in SEQ ID NO: 28; or a human monoclonal antibody or functional fragment thereof, the light chain variable region comprising an amino acid sequence as set out in SEQ ID NO. 19 and a heavy chain variable region comprising an amino acid sequence as set out in SEQ ID NO: 29; or a human monoclonal antibody or functional fragment thereof, the light chain variable region comprising an amino acid sequence as set out in SEQ ID NO. 19 and a heavy chain variable region comprising an amino acid sequence as set out in SEQ ID NO: 30; or a human monoclonal antibody or functional fragment thereof, the light chain variable region comprising an amino acid sequence as set out in SEQ ID NO. 19 and a heavy chain variable region comprising an amino acid sequence as set out in SEQ ID NO: 31; or a human monoclonal antibody or functional fragment thereof, the light chain variable region comprising an amino acid sequence as set out in SEQ ID NO. 19 and a heavy chain variable region comprising an amino acid sequence as set out in SEQ ID NO: 32; or a human monoclonal antibody or functional fragment thereof, the light chain variable region comprising an amino acid sequence as set out in SEQ ID NO. 19 and a heavy chain variable region comprising an amino acid sequence as set out in SEQ ID NO: 33; or a human monoclonal antibody or functional fragment thereof, the light chain variable region comprising an amino acid sequence as set out in SEQ ID NO. 19 and a heavy chain variable region comprising an amino acid sequence as set out in SEQ ID NO: 52; or a human monoclonal antibody or functional fragment thereof, the light chain variable region comprising an amino acid sequence as set out in SEQ ID NO. 19 and a heavy chain variable region comprising an amino acid sequence as set out in SEQ ID NO: 53.

According to a further embodiment, the inhibitory human monoclonal anti-GM-CSF antibody or functional fragment thereof comprises in its light chain variable region an amino acid sequence as set out in SEQ ID NO. 54. Preferred is a human monoclonal antibody or functional fragment thereof, the light chain variable region comprising an amino acid sequence as set out in SEQ ID NO. 54 and a heavy chain variable region comprising an amino acid sequence as set out in SEQ ID NO: 20; or a human monoclonal antibody or functional fragment thereof, the light chain variable region comprising an amino acid sequence as set out in SEQ ID NO. 54 and a heavy chain variable region comprising an amino acid sequence as set out in SEQ ID NO: 21; or a human monoclonal antibody or functional fragment thereof, the light chain variable region comprising an amino acid sequence as set out in SEQ ID NO. 54 and a heavy chain variable region comprising an amino acid sequence as set out in SEQ ID NO: 22; or a human monoclonal antibody or functional fragment thereof, the light chain variable region comprising an amino acid sequence as set out in SEQ ID NO. 54 and a heavy chain variable region comprising an amino acid sequence as set out in SEQ ID NO: 23; or a human monoclonal antibody or functional fragment thereof, the light chain variable region comprising an amino acid sequence as set out in SEQ ID NO. 54 and a heavy chain variable region comprising an amino acid sequence as set out in SEQ ID NO: 24; or a human monoclonal antibody or functional fragment thereof, the light chain variable region comprising an amino acid sequence as set out in SEQ ID NO. 54 and a heavy chain variable region comprising an amino acid sequence as set out in SEQ ID NO: 25; or a human monoclonal antibody or functional fragment thereof, the light chain variable region comprising an amino acid sequence as set out in SEQ ID NO. 54 and a heavy chain variable region comprising an amino acid sequence as set out in SEQ ID NO: 26; or a human monoclonal antibody or functional fragment thereof, the light chain variable region comprising an amino acid sequence as set out in SEQ ID NO. 54 and a heavy chain variable region comprising an amino acid sequence as set out in SEQ ID NO: 27; or a human monoclonal antibody or functional fragment thereof, the light chain variable region comprising an amino acid sequence as set out in SEQ ID NO. 54 and a heavy chain variable region comprising an amino acid sequence as set out in SEQ ID NO: 28; or a human monoclonal antibody or functional fragment thereof, the light chain variable region comprising an amino acid sequence as set out in SEQ ID NO. 54 and a heavy chain variable region comprising an amino acid sequence as set out in SEQ ID NO: 29; or a human monoclonal antibody or functional fragment thereof, the light chain variable region comprising an amino acid sequence as set out in SEQ ID NO. 54 and a heavy chain variable region comprising an amino acid sequence as set out in SEQ ID NO: 30; or a human monoclonal antibody or functional fragment thereof, the light chain variable region comprising an amino acid sequence as set out in SEQ ID NO. 54 and a heavy chain variable region comprising an amino acid sequence as set out in SEQ ID NO: 31; or a human monoclonal antibody or functional fragment thereof, the light chain variable region comprising an amino acid sequence as set out in SEQ ID NO. 54 and a heavy chain variable region comprising an amino acid sequence as set out in SEQ ID NO: 32; or a human monoclonal antibody or functional fragment thereof, the light chain variable region comprising an amino acid sequence as set out in SEQ ID NO. 54 and a heavy chain variable region comprising an amino acid sequence as set out in SEQ ID NO: 33; or a human monoclonal antibody or functional fragment thereof, the light chain variable region comprising an amino acid sequence as set out in SEQ ID NO. 54 and a heavy chain variable region comprising an amino acid sequence as set out in SEQ ID NO: 52; or a human monoclonal antibody or functional fragment thereof, the light chain variable region comprising an amino acid sequence as set out in SEQ ID NO. 54 and a heavy chain variable region comprising an amino acid sequence as set out in SEQ ID NO: 53.

According to a further embodiment, the inhibitory human monoclonal anti-GM-CSF antibody or functional fragment thereof comprises in its light chain variable region an amino acid sequence as set out in SEQ ID NO. 55. Preferred is a human monoclonal antibody or functional fragment thereof, the light chain variable region comprising an amino acid sequence as set out in SEQ ID NO. 55 and a heavy chain variable region comprising an amino acid sequence as set out in SEQ ID NO: 20; or a human monoclonal antibody or functional fragment thereof, the light chain variable region comprising an amino acid sequence as set out in SEQ ID NO. 55 and a heavy chain variable region comprising an amino acid sequence as set out in SEQ ID NO: 21; or a human monoclonal antibody or functional fragment thereof, the light chain variable region comprising an amino acid sequence as set out in SEQ ID NO. 55 and a heavy chain variable region comprising an amino acid sequence as set out in SEQ ID NO: 22; or a human monoclonal antibody or functional fragment thereof, the light chain variable region comprising an amino acid sequence as set out in SEQ ID NO. 55 and a heavy chain variable region comprising an amino acid sequence as set out in SEQ ID NO: 23; or a human monoclonal antibody or functional fragment thereof, the light chain variable region comprising an amino acid sequence as set out in SEQ ID NO. 55 and a heavy chain variable region comprising an amino acid sequence as set out in SEQ ID NO: 24; or a human monoclonal antibody or functional fragment thereof, the light chain variable region comprising an amino acid sequence as set out in SEQ ID NO. 55 and a heavy chain variable region comprising an amino acid sequence as set out in SEQ ID NO: 25; or a human monoclonal antibody or functional fragment thereof, the light chain variable region comprising an amino acid sequence as set out in SEQ ID NO. 55 and a heavy chain variable region comprising an amino acid sequence as set out in SEQ ID NO: 26; or a human monoclonal antibody or functional fragment thereof, the light chain variable region comprising an amino acid sequence as set out in SEQ ID NO. 55 and a heavy chain variable region comprising an amino acid sequence as set out in SEQ ID NO: 27; or a human monoclonal antibody or functional fragment thereof, the light chain variable region comprising an amino acid sequence as set out in SEQ ID NO. 55 and a heavy chain variable region comprising an amino acid sequence as set out in SEQ ID NO: 28; or a human monoclonal antibody or functional fragment thereof, the light chain variable region comprising an amino acid sequence as set out in SEQ ID NO. 55 and a heavy chain variable region comprising an amino acid sequence as set out in SEQ ID NO: 29; or a human monoclonal antibody or functional fragment thereof, the light chain variable region comprising an amino acid sequence as set out in SEQ ID NO. 55 and a heavy chain variable region comprising an amino acid sequence as set out in SEQ ID NO: 30; or a human monoclonal antibody or functional fragment thereof, the light chain variable region comprising an amino acid sequence as set out in SEQ ID NO. 55 and a heavy chain variable region comprising an amino acid sequence as set out in SEQ ID NO: 31; or a human monoclonal antibody or functional fragment thereof, the light chain variable region comprising an amino acid sequence as set out in SEQ ID NO. 55 and a heavy chain variable region comprising an amino acid sequence as set out in SEQ ID NO: 32; or a human monoclonal antibody or functional fragment thereof, the light chain variable region comprising an amino acid sequence as set out in SEQ ID NO. 55 and a heavy chain variable region comprising an amino acid sequence as set out in SEQ ID NO: 33; or a human monoclonal antibody or functional fragment thereof, the light chain variable region comprising an amino acid sequence as set out in SEQ ID NO. 55 and a heavy chain variable region comprising an amino acid sequence as set out in SEQ ID NO: 52; or a human monoclonal antibody or functional fragment thereof, the light chain variable region comprising an amino acid sequence as set out in SEQ ID NO. 55 and a heavy chain variable region comprising an amino acid sequence as set out in SEQ ID NO: 53.

A preferred inhibitory human monoclonal anti-GM-CSF antibody or functional fragment thereof comprises in its light chain a variable region a CDR1 region comprising an amino acid sequence as set out in SEQ ID NO. 16, a CDR2 region having an amino acid sequence as set out in SEQ ID NO. 17 and a CDR3 having an amino acid sequence as set out in SEQ ID NO. 18 and comprises in its heavy chain variable region a CDR1 region comprising an amino acid sequence as set out in SEQ ID NO. 14, a CDR2 region having an amino acid sequence as set out in SEQ ID NO. 15 and a CDR3 having an amino acid sequence as set out in any of SEQ ID NOs. 1, 2, 3, 4, 5, 6, 7, 8, 9, 10, 11, 12, 13 or 56.

In a further preferred embodiment the antibody comprises in its light chain an amino acid sequence as set out in SEQ ID NO: 34 and in its heavy chain an amino acid sequence as set out in SEQ ID NO: 35; or in its light chain an amino acid sequence as set out in SEQ ID NO: 34 and in its heavy chain an amino acid sequence as set out in SEQ ID NO: 36; or in its light chain an amino acid sequence as set out in SEQ ID NO: 34 and in its heavy chain an amino acid sequence as set out in SEQ ID NO: 37; or in its light chain an amino acid sequence as set out in SEQ ID NO: 34 and in its heavy chain an amino acid sequence as set out in SEQ ID NO: 38; or in its light chain an amino acid sequence as set out in SEQ ID NO: 34 and in its heavy chain an amino acid sequence as set out in SEQ ID NO: 39; or in its light chain an amino acid sequence as set out in SEQ ID NO: 34 and in its heavy chain an amino acid sequence as set out in SEQ ID NO: 40; or in its light chain an amino acid sequence as set out in SEQ ID NO: 34 and in its heavy chain an amino acid sequence as set out in SEQ ID NO: 41; or in its light chain an amino acid sequence as set out in SEQ ID NO: 34 and in its heavy chain an amino acid sequence as set out in SEQ ID NO: 42; or in its light chain an amino acid sequence as set out in SEQ ID NO: 34 and in its heavy chain an amino acid sequence as set out in SEQ ID NO: 43; or in its light chain an amino acid sequence as set out in SEQ ID NO: 34 and in its heavy chain an amino acid sequence as set out in SEQ ID NO: 44; or in its light chain an amino acid sequence as set out in SEQ ID NO: 34 and in its heavy chain an amino acid sequence as set out in SEQ ID NO: 45; or in its light chain an amino acid sequence as set out in SEQ ID NO: 34 and in its heavy chain an amino acid sequence as set out in SEQ ID NO: 46; or in its light chain an amino acid sequence as set out in SEQ ID NO: 34 and in its heavy chain an amino acid sequence as set out in SEQ ID NO: 47; or in its light chain an amino acid sequence as set out in SEQ ID NO: 34 and in its heavy chain an amino acid sequence as set out in SEQ ID NO: 48.

The preferred embodiments above provide human monoclonal antibody molecules and/or functional fragments thereof which are especially advantageous as neutralizers of the activity of non-human primate and human GM-CSF. Human monoclonal antibodies or functional fragments thereof according to these especially preferred embodiments are highly advantageous for several reasons.

First, they recognize non-human primate and human GM-CSF highly specifically. That is to say that from a mixture of non-human primate GM-CSF with other non-human primate colony stimulating factors (for example non-human primate G-CSF and M-CSF), the binding molecules according to these especially preferred embodiments are highly discriminating for non-human primate GM-CSF, whereas the other colony stimulating factors in the same milieu are not recognized. The same applies mutatis mutandis to human GM-CSF. This means that a human monoclonal antibody or functional fragment thereof according to these embodiments, when administered to a human, will be expected to specifically bind to and neutralize only the desired target, whereas other undesired targets are neither bound nor neutralized. Ultimately, this leads to a high degree of predictability concerning the therapeutic mode of action in vivo.

Second, binders according to these especially preferred embodiments bind to non-human primate and human GM-CSF with extremely high affinity. $K_D$ values of from about $4\times10^{-9}$ M down to as low as about $0.04\times10^{-9}$ M, the latter corresponding to about 40 pM, have been observed for molecules of this class. Since the kinetic on-rate of such molecules in aqueous media is largely diffusion controlled and therefore cannot be improved beyond what the local diffusion conditions will allow under physiological conditions, the low $K_D$ arises primarily as a result of the kinetic off-rate, $k_{off}$, which for the highest affinity antibody binder is approximately $10^{-5}$ $s^{-1}$. This means that once the complex between a human monoclonal antibody or functional fragment thereof according to any of these embodiments on the one hand and GM-CSF on the other hand is formed, it does not readily, or at least does not quickly separate. For binding molecules intended as neutralizers of biological activity, these characteristics are highly advantageous since the desirable neutralizing effect will normally last only as long as the molecule, the biological activity of which is to be neutralized (here non-human primate and human GM-CSF) remains bound by the neutralizing binding molecule. So a neutralizing molecule which remains bound to its intended target for a long time will continue to neutralize for a correspondingly long time.

The high binding affinity of human monoclonal antibodies or functional fragments thereof to non-human primate and human GM-CSF has an additional advantage. Normally, antibodies or functional fragments thereof will be eliminated from the bloodstream of a patient in a size-dependent fashion, with smaller molecules being excreted and eliminated before larger ones. Since the complex of the two polypeptides—antibody or antibody fragment and bound GM-CSF—is obviously larger than the antibody alone, the low $k_{off}$ mentioned above has the effect that therapeutic neutralizer is excreted and eliminated from the patient's body more slowly than would be the case, were it not bound to GM-CSF. Thus, not only the magnitude of the neutralizing activity but also its duration in vivo is increased.

The neutralizing activity determined for binders according to the above embodiments is surprisingly high. As will be described in more detail herein below, GM-CSF-neutralizing activity was measured in vitro using a TF-1 growth inhibition assay (Kitamura, T. et al. (1989). J Cell Physiol 140, 323-34). As an indication of neutralizing potential, $IC_{50}$ values were measured, $IC_{50}$ representing the concentration of the human monoclonal antibody or functional fragment thereof according to any of these embodiments required to elicit a half-maximal inhibition of TF-1 cell proliferation. For the human monoclonal anti-GM-CSF antibodies or functional fragments thereof specified above an $IC_{50}$ value of approximately $3\times10^{-10}$ M, or about 0.3 nM was determined. The binding molecules are therefore highly potent neutralizers of the activity of non-human primate and human GM-CSF.

In summary, then, the human monoclonal anti-GM-CSF antibodies or functional fragments thereof exhibit a high degree of discrimination for the desired antigen, bind this antigen extremely tightly and for a long time and exhibit highly potent neutralizing activity for the long time they remain bound. At the same time, the long persistence of the binder-antigen complex slows elimination of this binder from the body, thereby lengthening the duration of the desired therapeutic effect in vivo.

Similar considerations also apply for a neutralizing/inhibitory monoclonal anti-IL-17 antibody.

In accordance with the invention, the term "pharmaceutical composition" relates to a composition for administration to a patient, preferably a human patient. Preferably, the pharmaceutical composition comprises suitable formulations of carriers, stabilizers and/or excipients. In a preferred embodiment, the pharmaceutical composition comprises a composition for parenteral, transdermal, intraluminal, intraarterial, intrathecal and/or intranasal administration or by direct injection into tissue. It is in particular envisaged that said composition is administered to a patient via infusion or injection. Administration of the suitable compositions may be effected by different ways, e.g., by intravenous, intraperitoneal, subcutaneous, intramuscular, topical or intradermal administration. The composition of the present invention may further comprise a pharmaceutically acceptable carrier. Examples of suitable pharmaceutical carriers are well known in the art and include phosphate buffered saline solutions, water, emulsions, such as oil/water emulsions, various types of wetting agents, sterile solutions, liposomes, etc. Compositions comprising such carriers can be formulated by well known conventional methods. These pharmaceutical compositions can be administered to the subject at a suitable dose. The dosage regimen will be determined by the attending physician and clinical factors. As is well known in the medical arts, dosages for any one patient depend upon many factors, including the patient's size, body surface area, age, the particular compound to be administered, sex, time and route of administration, general health, and other drugs being administered concurrently. Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, inert gases and the like. In addition, the pharmaceutical composition in accordance with the present invention might comprise proteinaceous carriers, like, e.g., serum albumin or immunoglobulin, preferably of human origin. It is envisaged that the pharmaceutical composition in accordance with the invention might comprise, in addition to the above described compounds further biologically active agents, depending on the intended use of the pharmaceutical composition. Such agents might be drugs acting on the gastro-intestinal system, drugs acting as cytostatica, drugs preventing hyperurikemia, drugs inhibiting immunoreactions (e.g. corticosteroids), drugs modulating the inflammatory response, drugs acting on the circulatory system and/or agents such as cytokines known in the art.

The biological activity of the pharmaceutical composition defined herein can be determined for instance by cytotoxicity assays, as described in the following examples, in WO 99/54440 or by Schlereth et al. (Cancer Immunol. Immunother. 20 (2005), 1-12). "Efficacy" or "in vivo efficacy" as used herein refers to the response to therapy by the pharmaceutical composition of the invention, using e.g. standardized NCI response criteria. The success or in vivo efficacy of the therapy using a pharmaceutical composition in accordance with the invention refers to the effectiveness of the composition for its intended purpose, i.e. the ability of the composition to cause its desired effect, i.e. depletion of pathologic cells, e.g. tumor cells. The in vivo efficacy may be monitored by established standard methods for the respective disease entities including, but not limited to white blood cell counts, differentials, Fluorescence Activated Cell Sorting, bone marrow aspiration. In addition, various disease specific clinical chemistry parameters and other established standard methods may be used. Furthermore, computer-aided tomography, X-ray, nuclear magnetic resonance tomography (e.g. for National Cancer Institute-criteria based response assessment), positron-emission tomography scanning, white blood cell counts, differentials, Fluorescence Activated Cell Sorting, bone marrow aspiration, lymph node biopsies/histologies, and various lymphoma specific clinical chemistry parameters (e.g. lactate dehydrogenase) and other established standard methods may be used.

Another major challenge in the development of drugs such as the pharmaceutical composition in accordance with the invention is the predictable modulation of pharmacokinetic properties. To this end, a pharmacokinetic profile of the drug candidate, i.e. a profile of the pharmacokinetic parameters that affect the ability of a particular drug to treat a given condition, is established. Pharmacokinetic parameters of the drug influencing the ability of a drug for treating a certain disease entity include, but are not limited to: half-life, volume of distribution, hepatic first-pass metabolism and the degree of blood serum binding. The efficacy of a given drug agent can be influenced by each of the parameters mentioned above.

"Half-life" means the time where 50% of an administered drug are eliminated through biological processes, e.g. metabolism, excretion, etc.

By "hepatic first-pass metabolism" is meant the propensity of a drug to be metabolized upon first contact with the liver, i.e. during its first pass through the liver.

"Volume of distribution" means the degree of retention of a drug throughout the various compartments of the body, like e.g. intracellular and extracellular spaces, tissues and organs, etc. and the distribution of the drug within these compartments.

"Degree of blood serum binding" means the propensity of a drug to interact with and bind to blood serum proteins, such as albumin, leading to a reduction or loss of biological activity of the drug.

Pharmacokinetic parameters also include bioavailability, lag time (Tlag), Tmax, absorption rates, more onset and/or Cmax for a given amount of drug administered.

"Bioavailability" means the amount of a drug in the blood compartment.

"Lag time" means the time delay between the administration of the drug and its detection and measurability in blood or plasma.

"Tmax" is the time after which maximal blood concentration of the drug is reached, and "Cmax" is the blood concentration maximally obtained with a given drug. The time to reach a blood or tissue concentration of the drug which is required for its biological effect is influenced by all parameters.

The term "toxicity" as used herein refers to the toxic effects of a drug manifested in adverse events or severe adverse events. These side events might refer to a lack of tolerability of the drug in general and/or a lack of local tolerance after administration. Toxicity could also include teratogenic or carcinogenic effects caused by the drug.

The terms "safety", "in vivo safety" or "tolerability" as used herein define the administration of a drug without inducing severe adverse events directly after administration (local tolerance) and during a longer period of application of the drug. "Safety", "in vivo safety" or "tolerability" can be evaluated e.g. at regular intervals during the treatment and follow-up period. Measurements include clinical evaluation, e.g. organ manifestations, and screening of laboratory abnormalities. Clinical evaluation may be carried out and deviating to normal findings recorded/coded according to NCI-CTC and/or MedDRA standards. Organ manifestations may include criteria such as allergy/immunology, blood/bone marrow, cardiac arrhythmia, coagulation and the like, as set forth e.g. in the Common Terminology Criteria for adverse events v3.0 (CTCAE). Laboratory parameters which may be tested include for instance haematology, clinical chemistry, coagulation profile and urine analysis and examination of other body fluids such as serum, plasma, lymphoid or spinal fluid, liquor and the like. Safety can thus be assessed e.g. by physical examination, imaging techniques (i.e. ultrasound, x-ray, CT scans, Magnetic Resonance Imaging (MRI), other measures with technical devices (i.e. electrocardiogram), vital signs, by measuring laboratory parameters and recording adverse events. The term "effective and non-toxic dose" as used herein refers to a tolerable dose of the bispecific single chain antibody as defined herein which is high enough to cause depletion of pathologic cells, tumor elimination, tumor shrinkage or stabilization of disease without or essentially without major toxic effects. Such effective and non-toxic doses may be determined e.g. by dose escalation studies described in the art and should be below the dose inducing severe adverse side events (dose limiting toxicity, DLT).

The present application includes some figures, which depict the following.

FIG. 1: The effect of treatments with GM-CSF neutralizing mAb 22E9 (A), IL-1β neutralizing mAb 1400.24.17 (B), and TNFα antagonist etanercept (C) on joint swelling in chronic SCW inflammation. Arthritis was induced as described in Methods. Treatments were given i.p. as 300 µg dose on days 14, 17, 21, and 24. Inflammation was measured by $^{99m}$Tc uptake into knees and expressed as right (arthritic knee)/left (PBS control knee) ratio. A ratio of >1.10 is considered as joint swelling. Groups are compared by the Mann-Whitney U-test (*0.05>p>0.01; **0.01>p>0.001); n=7 per group.

Figure 2:
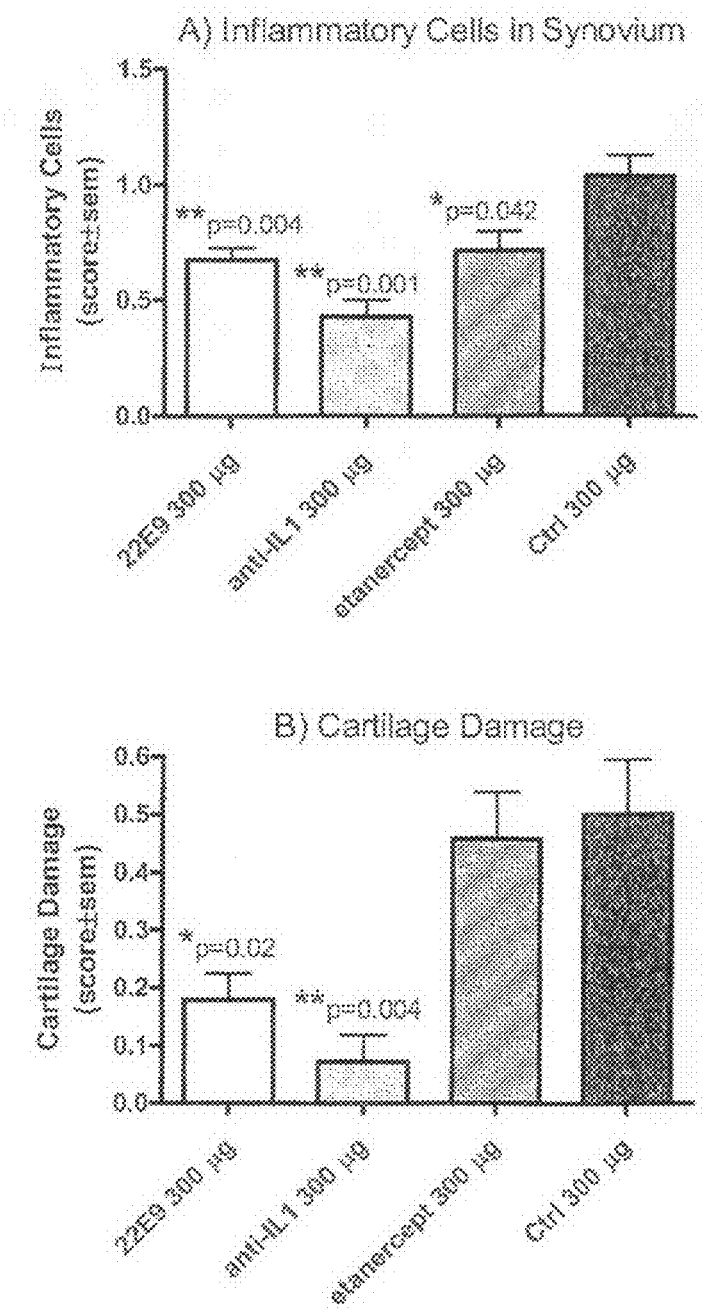

FIG. 2: The effect of treatments with GM-CSF neutralizing mAb (22E9 mAb), IL-1β neutralizing mAb (1400.24.17) and TNFα antagonist etanercept on influx of inflammatory cells into synovium (A), and on cartilage damage (B). Disease induction and treatments as described in Methods. Mice were euthanized on day 28 and histological sections were prepared and scored visually. Groups compared to control treatment by the Mann-Whitney U-test, n=7.

Figure 3:
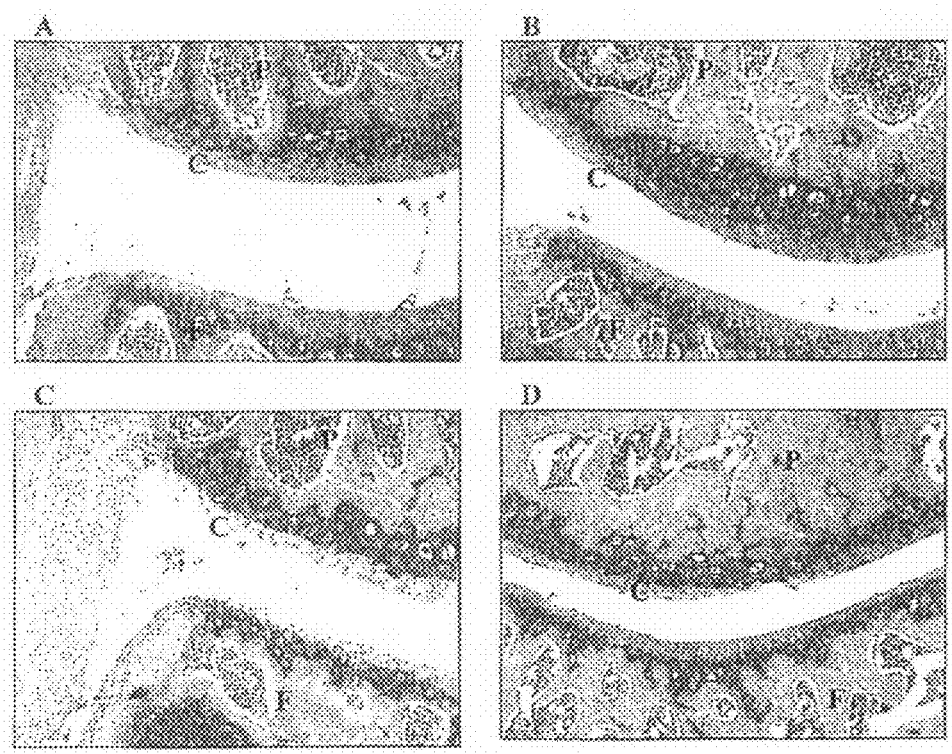

FIG. 3: The microphotographs of representative knees from mice with chronic SCW arthritis treated with GM-CSF neutralizing mAb (22E9) (A), α-IL-1β mAb (1400.24.17) (B), TNFα antagonist etanercept (C) and control mAb (D). Sections were made on day 28 post initial SCW arthritis induction and stained with Safranin O/fast green. P=patella; F=femur; C=cartilage. Note the well-preserved cartilage in (A) and (B), and cartilage proteoglycan loss and erosions in (C) and (D). The original magnification was 200×.

Figure 4:
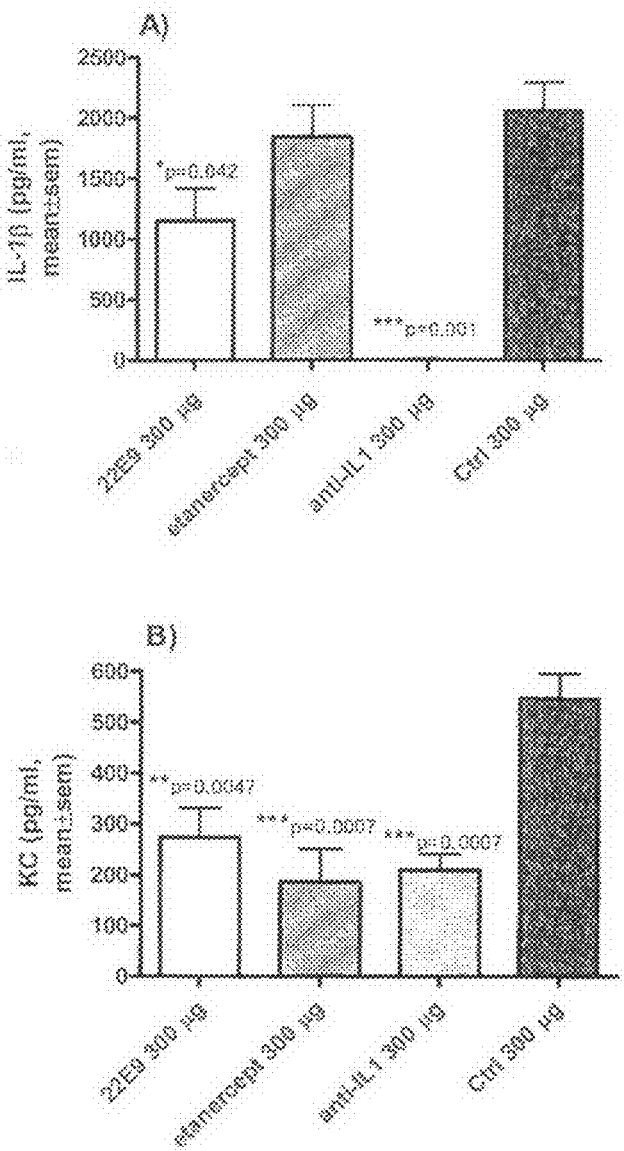

FIG. 4: The levels of local IL-1β (A) and KC (Groα equivalent) (B) measured by Luminex beads in supernatants from 1 hour-cultures of patellae established on day 21 post first induction of SCW arthritis. Treatments were performed as described in the legend to FIG. 1.

Figure 5:
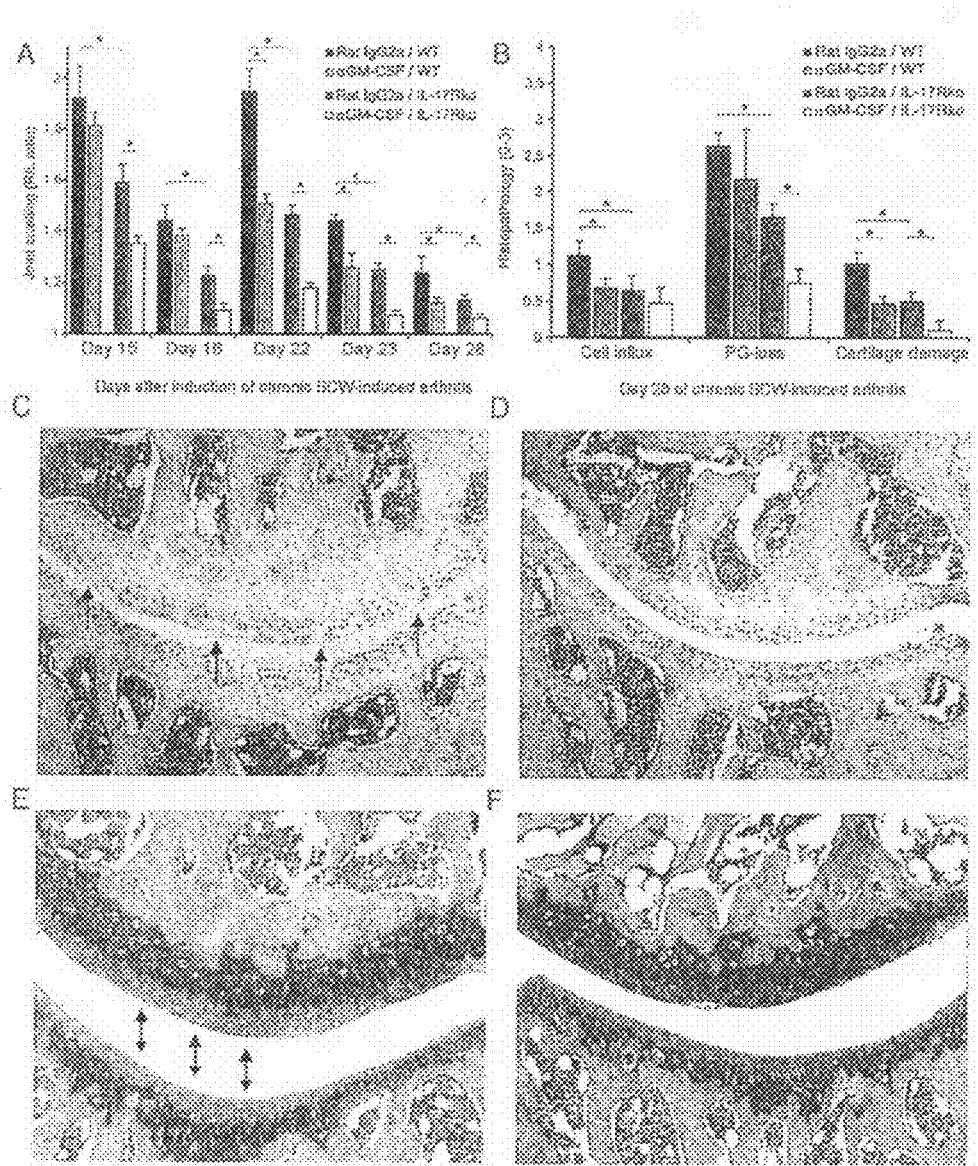

FIG. 5: Chronic SCW-induced arthritis in wild type and IL-17R-deficient mice treated with control antibodies or anti-GM-CSF. (A) Joint swelling in wild type (WT) and IL-17R−/− mice. As shown previously, significant differences were found in joint swelling between control-treated and anti-GM-CSF-treated mice at days 22, 23, and 28 in WT mice. (B) Joint inflammation and cartilage proteoglycan (PG) destruction at day 28. (C) Cartilage damage (erosions and chondrocyte death) in cartilage layers of the patella and femur of a WT mouse, treated with control antibody. (D) Reduced cartilage damage in an IL-17R−/− mouse treated with anti-GM-CSF antibodies. (E) Cartilage PG loss in the cartilage layers of the patella and femur of a WT mouse, treated with control antibody. (F) Cartilage PG loss in an IL-17R−/− mouse treated with anti-GM-CSF. For details see FIG. 3. Data are expressed as mean±SD of at least 6 mice per group. Experiments were repeated once with similar results. *P<0.01 compared to WT control mice treated with control antibodies, **P<0.01 compared to IL-17R−/− mice treated with anti-GM-CSF antibodies, Mann-Whitney U-test.

Figure 6:
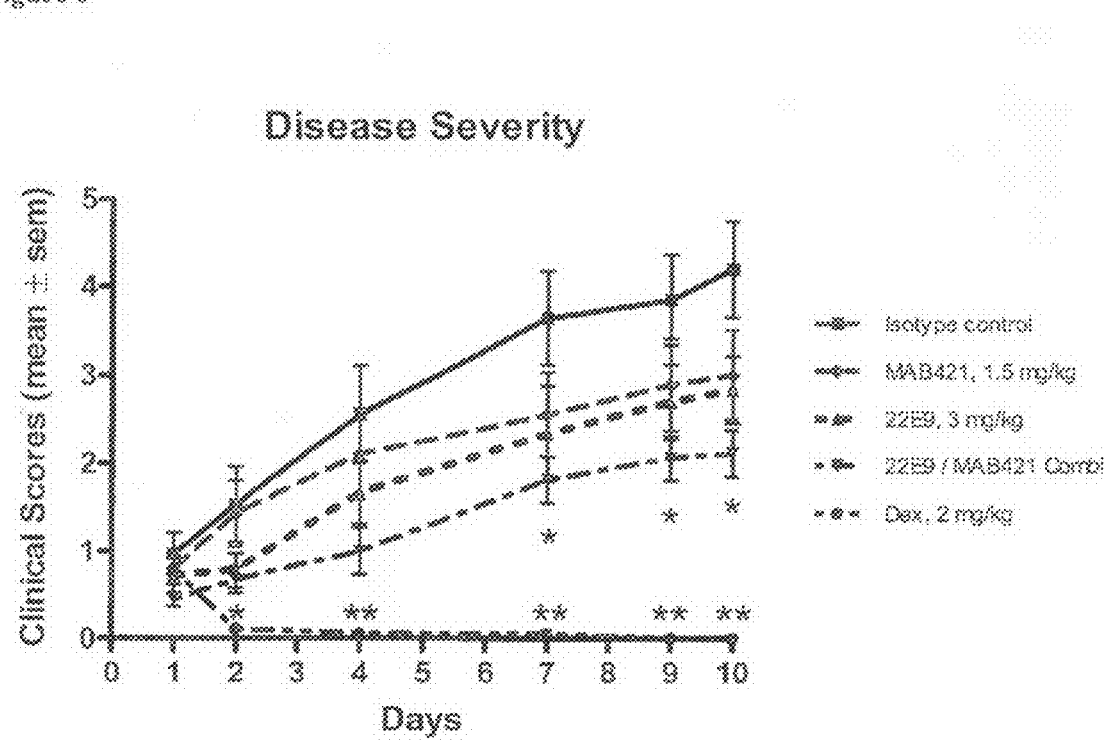

FIG. 6: Macroscopic scores of mice with collagen-induced arthritis, followed for ten days after start of treatment. Upon appearance of first symptoms of arthritis (corresponding to day 1 in FIG. 6), the mice were treated i.v. (also on day 1 in FIG. 6) with (i) one single administration of anti-IL17 monoclonal antibody: mAb421 1.5 mg/kg alone, (ii) anti-GM-CSF monoclonal antibody 22E9 3 mg/kg alone, or (iii) with mAb421 1.5 mg/kg and 22E9 3 mg/kg in combination. Blocking IL-17 with mAb421 in combination with neutralization of GM-CSF by using 22E9 significantly reduced clinical scores of collagen-induced arthritis, whereas treatment with mAb421 or 22E9 alone did not significantly decrease disease severity. The arthritic symptoms in the mice disappeared 2 to 3 days following i.p. administration of dexamethasone (2 mg/kg, positive control). An IgG2A antibody (isotype control) was used as a negative control. Results are mean+SEM of n=9-10 mice/group. *P<0.05, **P<0.01 vs. IgG2A isotype negative control-treated mice, determined by one-way ANOVA and Dunnett's multiple comparison test.

Figure 7:
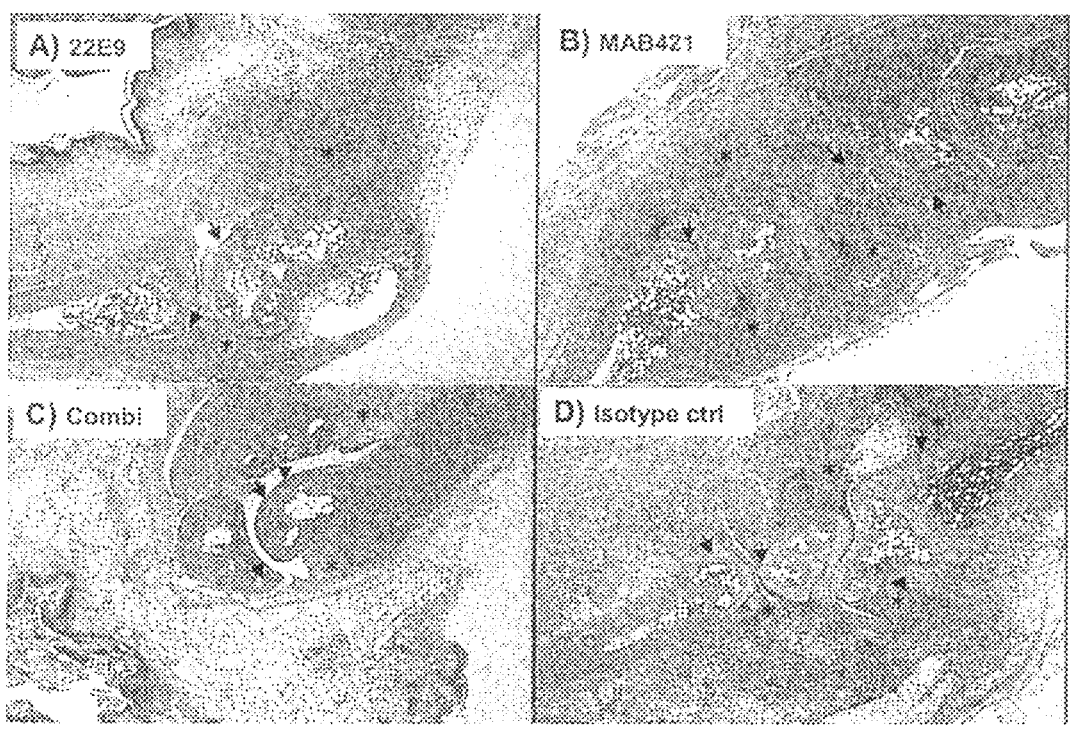

FIG. 7: Representative joint sections 10 days after a single administration of 22E9 3 mg/kg (A), mAb421 1.5 mg/kg (B), combination of 22E9 3 mg/kg and mAb 421 1.5 mg/kg (C), or the isotype control (D). Joints were fixed in 4% formalin, decalcified, sectioned and stained with haematoxylin/eosin. Mice receiving isotype control rat IgG2a (FIG. 7D) show marked joint inflammation with massive cellular infiltration in synovial membrane (*), and joint destruction with cartilage and bone erosions (↑). Although slightly less severe, mice receiving the dose of 22E9, 3 mg/kg (FIG. 7A) or mAb 421, 1.5 mg/kg (FIG. 7B), also show severe inflammation and joint destruction, whereas mice receiving a single administration of the combined treatment of 22E9 3 mg/kg together with mAb421 1.5 mg/kg, demonstrate very significantly reduced inflammation (*) (FIG. 7C) and good preservation of joint integrity with a near to normal cartilage surface shown by (↑) in FIG. 7C.

The following experimental details will enable the skilled person to exhaustively comprehend the gist of present invention.

Animals

Male C57Bl/6 mice were obtained from Charles River (Sulzfeld, Germany). IL-17R-deficient mice were kindly provided by J. Peschon, Amgen, Seattle, Wash., USA. The mice were housed in filter top cages, and water and food were provided ad libitum. The mice were used at an age of 10-12 weeks. All animal procedures were approved by the institutional ethics committee.

SCW Preparation and Induction of SCW Arthritis

Streptococcus pyogenes T12 organisms were cultured overnight in Todd-Hewitt broth. Cell walls were prepared as described by van den Broek et al., Am J Pathol 133(1), 139-149 (1988). The resulting 10,000×g supernatant was used throughout the experiments. The preparation contained 11% muramic acid. Unilateral arthritis was induced by intra-articular (i.a.) injection of 25 µg SCW (rhamnose content) in 6 µl phosphate buffered saline (PBS) into the right knee joint of naive mice, as described by Joosten et al., Ann Rheum Dis 59(3), 196-205 (2000). To create a chronic Streptococcal cell wall (SCW)-induced arthritis, i.a. injections into the right knee joint were performed at days 0, 7, 14, and 21. These repeated injections result in a chronic arthritis. As a control, PBS was injected into the left knee joint.

Reagents and Treatment Protocol

GM-CSF was neutralized using rat mAb 22E9 (MM500CS, Perbio Science, Bonn, Germany). Etanercept (Enbrel®; Wyeth Pharma, Münster, Germany) was used for TNFα blockade. Several studies have reported the effectiveness of this human soluble TNF receptor Fc fusion protein in different mouse models, including CIA. Rat IgG2a isotype control (BLD-400516-bulk, Biozol Diagnostica, Eching, Germany) and Humira® (Abbott, Wiesbaden-Delkenheim, Germany) were used as isotype controls. IL-1β was neutralized with the rat anti-mouse IL-1β mAb 1400.24.17

(MM425, Perbio Science, Bonn, Germany). All treatments administered i.p. as 300 µg doses were given 4 times: i) 2 hours prior to the 3rd reactivation (day 14), ii) on day 17, iii) 2 hours prior to the 4th reactivation (day 21), and iv) on day 24 after initial disease induction.

Measurement of Joint Swelling

Joint swelling during SCW arthritis was quantified by the $^{99m}$Tc-uptake method described by Kruijsen et al., Agents Actions 11(6-7), 640-2 (1981). This validated method measures by external gamma radiation counting the accumulation of radioisotope at the site of inflammation due to local increased blood flow and tissue swelling. The severity of swelling is expressed as the ratio of the $^{99m}$Tc-uptake in the right (inflamed) over the left (control) knee joint. All values exceeding 1.10 were considered as joint swelling.

Cytokine and Chemokine Measurements

Levels of several cytokines and chemokines, including IL-1β, IL-6, TNFα, RANTES, KC, and MIP-1α, were determined in patellae washouts. Patellae with surrounding synovial tissue were isolated from inflamed knee joints, and cultured in RPMI 1640 medium containing 0.1% BSA (200 µl/patella) for 1 hour at room temperature, as previously described by Joosten et al., J Immunol 165(11), 6553-8 (2000). Thereafter, supernatants were harvested and centrifuged for 5 minutes at 1000×g. Cytokine and chemokine levels were determined using the Luminex multi-analyte technology. We used the BioPlex system from BioRad (Munich, Germany) in combination with multiplex cytokine and chemokine kits.

Histological Analysis

Mice were sacrificed by cervical dislocation on day 28. Whole knee joints were removed and fixed in 4% formaldehyde for 7 days before decalcification in 5% formic acid and processing for paraffin embedding. Tissue sections (7 µm) were stained with haematoxylin/eosin (H/E) or safranin O/fast green (SO). Histopathological changes in the knee joints were scored in the patella/femur region on 5 semi-serial sections spaced 140 µm apart. Scoring was performed on coded slides by two separate observers, using the following parameters. In the H/E stained slides the amount of cells infiltrating the synovial lining was scored from 0-3. Cartilage damage was scored in the SO stained slides on a scale from 0-3.

Statistical Analysis

Differences between experimental groups were tested using the Mann-Whitney U test and using GraphPad Prism 4 software. Significance readouts were grouped as follows: *=0.05>p>0.01; =0.01>p>0.001; and *=p<0.001.

The following Examples will likewise enable the skilled person to exhaustively comprehend the gist of present invention.

EXAMPLE 1

Systemic GM-CSF Neutralization Decreases Joint Swelling in the Chronic SCW Model During the chronic phase of SCW arthritis in C57Bl/6 mice, the effect on joint swelling after treatment with biologicals neutralizing GM-CSF (mAb 22E9), TNFα (etanercept) or IL-1β (mAb 1400.24.17) was investigated on days 15, 16, 22, 23 and 28 by differential uptake of $^{99m}$Tc into the knee joints. Results are expressed as the ratio of $^{99m}$Tc uptake between the arthritic SCW-injected knee and the PBS-injected control knee.

Systemic administration of the GM-CSF-neutralizing antibody potently and significantly decreased joint swelling on days 16, 22, 23 and 28 with p-values of 0.018, 0.004, 0.004, and 0.002, respectively (FIG. 1A). IL-1β neutralization also decreased joint swelling, although a significant reduction in $^{99m}$Tc uptake of knees versus control knees was only seen on days 22 (p=0.011) and 23 (p=0.001) (FIG. 1B). As expected, TNFα blockade with etanercept, which is able to neutralize human as well murine TNFα had no effect on joint swelling in the chronic SCW model (FIG. 1C). In contrast, etanercept was previously shown to be active in the acute phase of this disease model. Neutralization of GM-CSF during chronic SCW arthritis thus appeared to be more potent than neutralization of IL-1β, and its effect was sustained until day 28, i.e., 4 days after the last administration of the antibody. A second independent study confirmed the efficacy of GM-CSF neutralization on decreasing joint swelling in the chronic SCW model.

EXAMPLE 2

GM-CSF Neutralization Reduces Inflammatory Cell Influx to Synovium, and Cartilage Damage Histopathological sections from joints of the different groups of mice were prepared after termination of the experiment on day 28. The extent of inflammatory cell influx into synovium and assessment of cartilage damage were independently scored by two investigators on blinded H/E- and SO-stained tissue sections.

All three treatments, GM-CSF neutralization with mAb 22E9, IL-1β neutralization with mAb1400.24.17 and TNFα blockade with etanercept were efficacious at significantly reducing the influx of inflammatory cells into the synovium (FIG. 2A). TNFα blockade, although significantly effective, appeared less potent than GM-CSF or IL-1β neutralization with p-values vs. controls of 0.042, 0.004, and 0.001, respectively. Furthermore, despite a reduction of inflammatory cell influx in knee joints of etanercept-treated mice, cartilage integrity was not preserved (FIG. 2B). In contrast, GM-CSF neutralization significantly protected from cartilage damage (p=0.02; mAb 22E9 vs. isotype control mAb) (FIG. 2B). As previously reported, IL-1β neutralization was very potent at protecting cartilage from damage (p=0.004, anti-IL-1β vs. control; FIG. 2B).

The impact of the various treatments on cartilage integrity are illustrated in FIG. 3 showing microphotographs of Safranin O/fast green staining of knee joints from one representative mouse for each of the three treatment groups. The robust cartilage staining and good tissue preservation observed in the mAb 22E9-treated mouse (FIG. 3A) highlights the effect of GM-CSF neutralization on protecting cartilage integrity. In contrast, cartilage from the mouse receiving the isotype control antibody (FIG. 3D) shows destructive erosions and reduced staining intensity demonstrating loss of proteoglycan, one of the major components of articular cartilage. Similarly, loss of proteoglycan and increased cartilage damage is seen in the etanercept-treated mouse (FIG. 3C). This is consistent with earlier studies in the chronic SCW model of arthritis showing independence of TNFα. IL-1β is known to have a prominent destructive effect on cartilage in experimental models of arthritis. Accordingly, neutralization of IL-1β by an antibody has a pronounced protective effect on cartilage in our present study (FIG. 3B).

EXAMPLE 3

GM-CSF Neutralization Reduces Production of IL-1β and KC in Knee Joints

In order to better understand the protective effect of GM-CSF and its relationship to IL-1β we investigated concentrations of various cytokines and chemokines in patella washouts. Only the arthritic (right) knees were analyzed as levels in the non-affected control knees (left) have been repeatedly found to be below the limit of detection in previous experiments.

GM-CSF neutralization with mAb 22E9 resulted in a significant reduction of local IL-1β in comparison to the levels detected in joints from mice receiving the isotype control antibody treatment (p=0.042; 22E9-treated vs. control) (FIG. 4). TNFα blockade with etanercept had no effect on the levels of IL-1β in joints (FIG. 4) whereas, and as expected, in mice having received IL-1β-neutralizing mAb, levels of IL-1β were close to base line. Levels of the chemokine KC (mouse GRO-α) were significantly reduced in the arthritic knee joints by all three treatments (p=0.0047 for 22E9 vs. control; p=0.0007 for etanercept vs. control; p=0.007 for anti-IL-1β vs. control). Local levels of IL-6 and RANTES were not influenced by any of the treatments investigated (data not shown). Levels of IL-2, TNFα and GM-CSF were below the detection limits of the assays, e.g., <10 pg/ml.

EXAMPLE 4

GM-CSF Neutralization in the Absence of IL-17 Signaling Potentiates the Protective Effects on Cartilage Destruction GM-CSF neutralization decreased joint swelling and protected cartilage from damage with an efficacy similar to that observed with IL-10 neutralization. Subsequently, similar studies with anti-GM-CSF mAb in chronic SCW arthritis were performed in mice deficient for IL-17R. IL-17R-deficiency results in suppressed joint swelling and cartilage destruction during chronic SCW arthritis (FIG. 5A). Combined targeting of both GM-CSF and IL-17 signaling in this arthritis model resulted in a strong, enhanced suppression of joint swelling (FIG. 5A). Although both anti-GM-SCF treatment as well as IL-17R-deficiency resulted in reduced cell influx, combined targeting did not result in significantly less joint inflammation (FIG. 5B). Interestingly, however, proteoglycan depletion and cartilage damage (chondrocyte death and erosion) were markedly reduced in anti-GM-CSF treated IL-17R-deficient mice. (FIG. 5B-E). These results demonstrate that the protective effect on cartilage of anti-GM-CSF can be further enhanced by the additional targeting of the T cell cytokine IL-17.

EXAMPLE 5

The chronic relapsing SCW mouse model of arthritis is characterized by a severe destruction of joints as is typical in later stages of chronic RA in humans. In contrast to what is observed in the CIA mouse model and the acute SCW model of arthritis, TNFα neutralization is no longer effective in controlling chronic SCW arthritis in which IL-1β appears to play the major pathogenic role (72). The TNFα independence and a key role for IL-1β in cartilage destruction in chronic SCW arthritis have been confirmed in our study.

GM-CSF blockade was studied for the first in this particular model and found to have a profound inhibitory effect on joint swelling and cartilage destruction in SCW-injected knees when doses of 300 μg antibody were administered i.p. in the chronic phase of disease. This demonstrates that an anti-GM-CSF antibody in mice at a dose, which is equivalent to an antibody dose of approximately 1 mg/kg in humans (after allometric correction), is sufficient to correct GM-CSF levels in arthritic knee joints. The therapeutic efficacy of GM-CSF neutralization in the chronic arthritis model was profound. Joint swelling was better controlled by anti-GM-CSF than by anti-IL-1β treatment while TNFα blockade was ineffective. Aberrant TNFα-production may still play some role in chronic SCW arthritis because its neutralization had an effect on influx of inflammatory cells and KC chemokine levels. However, the role of TNFα in driving this chronic disease is diminished as opposed to the acute phase of the disease, and in contrast to other mouse models of arthritis. With respect to cartilage protection, both anti-GM-CSF and anti-IL-1β treatments were very effective. Interdependence between the actions of GM-CSF and IL-1 has been reported previously in another model of arthritis. In this model of IL-1-induced arthritis following mBSA injection, GM-CSF plays a preponderant pathogenic role. Absence of GM-CSF as in GM-CSF KO mice, or by GM-CSF neutralization in WT animals, markedly reduced arthritis. During the chronic SCW arthritis, however, GM-CSF seems to act upstream of IL-1β, since its neutralization reduced IL-1β levels in the arthritic joints. This reduced IL-1 production by activated macrophages and other GM-CSF-stimulated immune cells might also explain why anti-GM-CSF treatment had a protective effect on cartilage in our model. In the acute SCW model, we also found that anti-GM-CSF antibody could reduce IL-1β levels, while the TNFα blocker etanercept could not. In the CIA mouse model of RA, GM-CSF blockade reduced both the levels of IL-1β and TNFα in a very significant way.

While GM-CSF expression is acutely induced in various immune cells by pro-inflammatory cytokines such as TNFα and IL-1β through activation of transcription factor NF-kappaB and others, the hierarchy of cytokines appears to flip in later stages of inflammation, with GM-CSF taking over control of TNFα and IL-1β production, and perhaps of other cytokines and chemokines. Simultaneously to the inhibition of TNFα and IL-1β in arthritic tissue, GM-CSF blockade also has the potential to reduce the activity and survival of GM-CSF-dependent immune cells, such as granulocytes, neutrophils, macrophages. It is conceivable that GM-CSF not only directly induces IL-1β and TNFα expression, but also causes a coordinated anti-apoptotic action and a continuous activation of multiple cells of the innate immune system, thereby indirectly enhancing IL-1β and TNFα production. Such an effect on cell cycling and survival has been demonstrated in the mBSA arthritis model in which GM-CSF neutralization in vivo resulted in markedly reduced overall cellularity as well as number of cycling cells in the arthritic joints.

EXAMPLE 6

In addition to blocking GM-CSF during chronic SCW arthritis in WT animals, experiments were also performed in IL-17R-deficient mice. IL-17 is produced by Th17 cells, which can simultaneously produce TNFα and GM-CSF. In the presence of TNFα, IL-17 triggers synoviocytes to produce GM-CSF, suggesting a role for IL-17 upstream of GM-CSF. On the other hand, GM-CSF-treated bone marrow cells stimulated with LPS produce IL-23, which is an important survival factor for IL-17-producing Th17 cells. Prior to the present invention, combined blocking of IL-17 and GM-CSF had not been studied in vitro or in vivo. The present study of the inventors is first to show that simultaneous blockade of both GM-CSF and IL-17 pathways resulted in superior suppression of joint swelling and increased protection to cartilage destruction relative to blockade of single pathways. This strong effect on cartilage might be explained by a synergy between IL-17 and (GM-CSF-induced) IL-1β, since these two cytokines have previously shown synergy on cytokine production by synovium from RA patients and on $PGE_2$ and NO production in osteoarthritic cartilage. The present and previous studies make a strong point that neutralization of GM-CSF may have therapeutic potential in human RA patients also in patients that are no longer, or have initially not been responsive to TNFα blockade. In addition, this study demonstrates that anti-GM-CSF in combination with anti-IL-17 treatment has a profound therapeutic effect in RA as well as in other autoimmune and inflammatory disease settings.

EXAMPLE 7

Collagen-induced arthritis (CIA) is a widely accepted arthritis mouse model based on T cell- and antibody-mediated autoimmune reactivity against cartilage collagen type II (CII). This model shares several clinical, histopathological and immunological features with human RA, and is mainly characterized by synovial inflammation followed by severe cartilage and bone erosions. The objective of the present study described here was the evaluation of the therapeutic efficacy of the combined administration of a GM-CSF neutralizing compound and an IL-17 neutralizing compound in the CIA mouse model system. In particular, the effect of the treatment of mice with (i) an anti-IL-17 monoclonal antibody (mAb 421) alone, (ii) an anti-GM-CSF monoclonal antibody (mAb 22E9) alone, and (iii) a combination of both antibodies was studied after the onset of CIA, in comparison to negative (IgG2A) and positive (dexamethasone) controls. Anti-IL-17 antibody mAb421 was obtained from R&D Systems, whereas mAb 22E9 was from Perbio Science. Rat IgG2a isotype control antibodies were derived from Biolegend. All antibodies were stored at −80° C. Dexamethasone was derived from Centrafarm and stored at room temperature. All compounds were diluted in sterile PBS for administration.

The effect of treatment with the above-indicated compounds on CIA mice was studied in a 7-week study design. On day 0, male DBA/1J mice were immunized at the base of the tail with 100 µg of bovine CII under isoflurane anesthesia. On day 21, the mice received an intraperitoneal booster injection of 100 µg of CII dissolved in phosphate-buffered saline (PBS), and the onset of arthritis occurred a few days after this booster injection. Bovine type II collagen (CII) at a concentration of 2 mg/ml in 0.05M acetic acid was emulsified in equal volumes of Freund's complete adjuvant (2 mg/ml of *Mycobacterium tuberculosis* strain H37Ra). At first symptoms of arthritis (score 0.25 or more), mice were sequentially assigned to the different experimental groups listed below and were observed for another 10 days of study.

Mice were considered to have arthritis when significant changes of redness and/or swelling were noted in the digits or in other parts of the paws. Joint inflammation in each paw was scored visually, using a scale of 0-2 per paw with a maximal score of 8 per animal (four paws with arthritic symptoms and a scale of up to 2 each), as described by R. Smeets et al, Arthritis Rheum 2003: 0=no inflammation, 1=mild inflammation, 1.5=marked inflammation, and 2=severe inflammation. Scoring was performed three times a week from day 21 till day 45 by independent observers without knowledge of the experimental groups.

Antibodies were administered as one single dose on onset of arthritis symptoms. Dexamethasone was given at a dose of 2 mg/kg, i.p. three times a week (on Monday, Wednesday, and Friday). Mice that had not displayed any symptoms of arthritis by day 35 of the study were considered non-responders and were removed from further study analysis.

Based on the results of previous experiments, the dose for the study was set at 1.5 mg/kg mAb421. For anti-GM-CSF antibody 22E9, the dose was set at 3 mg/kg. With these dosages, the study was performed to evaluate the effect of combined blocking of IL-17 and GM-CSF during collagen-induced arthritis. Dexamethasone was used as a positive control and a rat IgG2a antibody as a negative control. In addition, the study included experimental groups for treatment with anti-IL-17 (mAb421), anti-GM-CSF (22E9), and their combination, all in the indicated doses.

Experimental Groups:
mAb421 1.5 mg/kg+Rat IgG2a 3 mg/kg (total 4.5 mg/kg)
22E9 3 mg/kg+Rat IgG2a 1.5 mg/kg
mAb421 1.5 mg/kg+22E9 3 mg/kg
Rat IgG2a 15 mg/kg
Dexamethasone 2 mg/kg As shown in FIG. 6, neutralization of IL-17 with mAb421 in combination with neutralization of GM-CSF by using 22E9 significantly reduced clinical scores of collagen-induced arthritis. In contrast, treatment with mAb421 or 22E9 alone did not significantly decrease disease severity.

The arthritic symptoms disappeared 2 to 3 days after i.p. administration of dexamethasone (2 mg/kg, positive control). IgG2A antibody-treated mice (negative control) showed a clear progression of arthritis severity.

For histopathologic analysis, front and hind paws (left and right; 4 samples/mouse) were delivered. The paws were fixed in 4% formaldehyde solution. After decalcification in EDTA or standard decalcification solution for 3 days, paws were embedded in paraffin (Paraplast®), stained with H&E, and evaluated by light microscope. The histological evaluation was restricted to the distal joints (tarsus/carpus and digits) of the paws.

Histological evaluation revealed a subacute to chronic arthritis of the lower joints of the limbs (carpal/tarsal, digits). The arthritis was characterised by thickening of the synovium (synovial hyperplasia), intraarticular exudate and a prominent mixed cell infiltration predominantly in the capsule of the joint. In the marked cases the inflammatory cell reaction was also seen in the connective tissue and tendons. Additionally, in more chronic cases a typical granulation tissue consisting of fibrous tissue and mainly mononuclear cells was observed. Erosive changes of the cartilage of the distal joints were also seen. In most cases more than one joint was affected (polyarthritis). FIG. 7 shows representative joint sections 10 days after a single administration of 22E9 3 mg/kg (A), mAb421 1.5 mg/kg (B), combination of 22E9 3 mg/kg and mAb 421 1.5 mg/kg (C), or the isotype control 15 mg/kg (D). Joints were fixed in 4% formalin, decalcified, sectioned and stained with haematoxylin/eosin. Mice receiving isotype control (FIG. 7D) showed marked joint inflammation with massive cellular infiltration in synovial membrane, and joint destruction with cartilage and bone erosions. Although slightly less severe, mice receiving 22E9, 3 mg/kg (FIG. 7A) or mAb 421, 1.5 mg/kg (FIG. 7B), also showed severe inflammation and joint destruction, whereas mice receiving a single administration of the combined treatment of 22E9 3 mg/kg together with mAb421 1.5 mg/kg, demonstrated very significantly reduced inflammation and good preservation of joint integrity with a near to normal cartilage surface (FIG. 7C). As a result, most cases with arthritis were seen in the negative control group (Rat IgG2A). No arthritis could be detected after 2 to 3 days after administration of dexamethasone (positive control). Comparing the CIA mice treated with mAb421 or mAb 22E9 alone, or in combination, to negative controls, best results regarding occurrence and severity of arthritis were seen in the group treated by mAb421 in combination with mAb22E9.

Conclusion:

The present inventors explored the therapeutic efficacy of GM-CSF neutralization in two different arthritis model systems, i.e. (i) the TNFα-independent chronic SCW arthritis model and (ii) the TNFα-dependent CIA model. In addition, they studied the effect of blocking both innate and adaptive immunity by inhibiting the GM-CSF and IL-17 pathways. This was performed by neutralizing GM-CSF in mice genetically deficient for IL-17 receptor (IL-17R-KO mice) or by combination treatment with monoclonal antibodies neutralizing GM-CSF and IL-17. The inventors unexpectedly observed that both types of inflammatory diseases can be treated in a highly effective manner, by the combined blockade of GM-CSF and IL-17 pathways. In the CIA model, the combined administration of a GM-CSF inhibiting compound and an IL-17 inhibiting compound significantly reduced clinical scores of collagen-induced arthritis, whereas treatment with the GM-CSF inhibiting compound or the IL-17 inhibiting compound alone did not significantly decrease the severity of arthritis. In addition, a detailed histological analysis demonstrated the beneficial effect of the combination therapy on joint inflammation and destruction of cartilage and bone. Thus, the combined blockade of both pathways resulted in a highly efficient protection from inflammation and joint destruction. These results were particularly surprising as, up to very recently, it was hypothesized that GM-CSF lies downstream of IL-17 (see e.g. Kawaguchi M. et al., J. Allergy Clin. Immunol. 114 (2004), 444-450; Starnes T. et al., The Journal of Immunology 169 (2002), 642-646; Laan M. et al., Eur. Respir. J. 21 (2003), 387-393). Therefore, no additive or synergetic effects could have been expected from treatments combining the blockade of these two pathways. The present application is first to demonstrate the advantageous effects of combined blocking of IL-17 and GM-CSF in vivo. Simultaneous blockade of both IL-17 and GM-CSF pathways resulted in superior suppression of joint swelling and increased protection to cartilage destruction relative to blockade of single pathways. The data presented here make a strong point that anti-GM-CSF in combination with anti-IL-17 treatment does not only have a profound therapeutic effect in RA but also in other autoimmune and inflammatory disease settings, as defined herein above.

The invention claimed is:

1. A method for the treatment of rheumatoid arthritis in a subject suffering therefrom, the method comprising administering to said subject an effective amount of
   (a) an antibody or a fragment thereof that binds to GM-CSF or GM-CSF receptor and inhibits or prevents the binding of GM-CSF to the GM-CSF receptor; and
   (b) an antibody or a fragment thereof that binds to IL-17 or IL-17 receptor and inhibits or prevents the binding of IL-17 to the IL-17 receptor.

2. The method according to claim 1, wherein
   (a) the antibody or fragment thereof that binds to GM-CSF or GM-CSF receptor is administered prior to the antibody or fragment thereof that binds to IL-17 or IL-17 receptor;
   (b) the antibody or fragment thereof that binds to GM-CSF or GM-CSF receptor is administered subsequent to the antibody or fragment thereof that binds to IL-17 or IL-17 receptor; or
   (c) the antibody or fragment thereof that binds to GM-CSF or GM-CSF receptor and the antibody or fragment thereof that binds to IL-17 or IL-17 receptor are administered simultaneously.

3. The method according to claim 1, wherein the subject is a human or a non-human primate.

4. The method according to claim 1, wherein the antibody or the fragment thereof that binds to GM-CSF or GM-CSF receptor is an antibody or fragment thereof that binds to an epitope of GM-CSF, the epitope comprising amino acids 23-27 (RRLLN) of SEQ ID NO: 57, 58, 59 or 60 and/or amino acids 65-77 (GLR/QGSLTKLKGPL) of SEQ ID NO: 57, 58, 59 or 60.

5. The method according to claim 4, wherein said epitope further comprises:
   (a) amino acids 28-31 (LSRD) of SEQ ID NO: 57, 58, 59 or 60;
   (b) amino acids 32-33 (TA) of SEQ ID NO: 57, 58, 59 or 60; and/or
   (c) amino acids 21-22 (EA) of SEQ ID NO: 57, 58, 59 or 60.

6. The method according to claim 1, wherein the antibody or fragment thereof that binds to GM-CSF is a human monoclonal antibody or a fragment thereof.

7. The method according to claim 6, wherein said antibody or fragment thereof comprises in its light chain variable region a CDR1 comprising an amino acid sequence as set out in SEQ ID NO: 16, a CDR2 comprising an amino acid sequence as set out in SEQ ID NO: 17 and a CDR3 comprising an amino acid sequence as set out in SEQ ID NO: 18; and comprises in its heavy chain variable region a CDR1 region comprising an amino acid sequence as set out in SEQ ID NO: 14, a CDR2 region comprising an amino acid sequence as set out in SEQ ID NO: 15 and a CDR3 comprising an amino acid sequence as set out in SEQ ID NO: 2.

8. The method according to claim 7, wherein said antibody or fragment thereof comprises in its light chain variable region an amino acid sequence as set out in any of SEQ ID NO: 19, 54 and 55.

9. The method according to claim 7, wherein said antibody or fragment thereof comprises in its heavy chain variable region an amino acid sequence as set out in any of SEQ ID NO: 21 or 52.

10. The method according to claim 7, wherein said antibody or fragment thereof comprises in its light chain variable region an amino acid sequence as set out in SEQ ID NO: 19 and in its heavy chain variable region an amino acid sequence as set out in SEQ ID NO: 21.

11. The method according to claim 7, wherein said antibody or fragment thereof comprises a light chain amino acid sequence as set out in SEQ ID NO: 34 and a heavy chain amino acid sequence as set out in SEQ ID NO: 35.

12. The method according to claim 1, wherein the antibody or fragment thereof that binds to IL-17 is a human monoclonal antibody or a fragment thereof.

* * * * *